US009937130B2

(12) United States Patent
McDonnell et al.

(10) Patent No.: US 9,937,130 B2
(45) Date of Patent: *Apr. 10, 2018

(54) SUSTAINED DELIVERY OF THERAPEUTIC AGENTS TO AN EYE COMPARTMENT

(71) Applicant: The Johns Hopkins University, Baltimore, MD (US)

(72) Inventors: Peter J. McDonnell, Baltimore, MD (US); Yasin A. Khan, Baltimore, MD (US); Samuel K. Lai, Carrboro, NC (US); Renata T. Kashiwabuchi, Baltimore, MD (US); Ashley Behrens, Baltimore, MD (US); Justin S. Hanes, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/138,132

(22) Filed: Apr. 25, 2016

(65) Prior Publication Data
US 2016/0235674 A1 Aug. 18, 2016

Related U.S. Application Data

(63) Continuation of application No. 14/521,904, filed on Oct. 23, 2014, now Pat. No. 9,566,242, which is a
(Continued)

(51) Int. Cl.
*A61K 9/00* (2006.01)
*A61K 9/16* (2006.01)
(Continued)

(52) U.S. Cl.
CPC .......... *A61K 9/1676* (2013.01); *A61K 9/0048* (2013.01); *A61K 9/0051* (2013.01);
(Continued)

(58) Field of Classification Search
CPC ...... A61K 31/519; A61K 31/52; A61K 45/06; A61K 47/48176; A61K 47/48215;
(Continued)

(56) References Cited

U.S. PATENT DOCUMENTS 4,027,676 A 6/1977 Mattei
4,201,216 A 5/1980 Mattei
(Continued)

FOREIGN PATENT DOCUMENTS

EP 1752142 9/2009
WO 9207866 5/1992
(Continued)

OTHER PUBLICATIONS

Zimmer et al. (Advanced Drug Delivery Reviews 16 (1995) 61-73).*

(Continued)

*Primary Examiner* — Aradhana Sasan
(74) *Attorney, Agent, or Firm* — Pabst Patent Group LLP

(57) ABSTRACT

Compositions and methods for treating eye disorders by administering a drug delivery system into an eye compartment of the patient, wherein the drug delivery system contains a particle containing a core; a coating associated with the particle, wherein the coating is covalently or non-covalently associated with the particle and presents a hydrophilic region to the environment around the particle; and a therapeutic agent are disclosed. The eye compartment can exhibit reduced inflammation or IOP after administration of the drug delivery systems to a patient than if a drug delivery system including an uncoated particle were administered to the patient.

69 Claims, 1 Drawing Sheet

Related U.S. Application Data continuation of application No. 13/581,454, filed as application No. PCT/US2011/026321 on Feb. 25, 2011, now Pat. No. 8,889,193.

(60) Provisional application No. 61/308,053, filed on Feb. 25, 2010, provisional application No. 61/308,042, filed on Feb. 25, 2010, provisional application No. 61/308,035, filed on Feb. 25, 2010.

(51) Int. Cl.

| | | |
|---|---|---|
| *A61K 9/50* | (2006.01) | |
| *A61K 31/52* | (2006.01) | |
| *A61K 31/519* | (2006.01) | |
| *A61K 45/06* | (2006.01) | |
| *A61K 9/51* | (2006.01) | |
| *A61K 47/48* | (2006.01) | |

(52) U.S. Cl.
CPC .......... *A61K 9/1641* (2013.01); *A61K 9/1647* (2013.01); *A61K 9/5026* (2013.01); *A61K 9/5031* (2013.01); *A61K 9/5146* (2013.01); *A61K 9/5153* (2013.01); *A61K 31/519* (2013.01); *A61K 31/52* (2013.01); *A61K 45/06* (2013.01); *A61K 47/48176* (2013.01); *A61K 47/48215* (2013.01)

(58) Field of Classification Search
CPC .. A61K 9/0048; A61K 9/0051; A61K 9/1641; A61K 9/1647; A61K 9/1676; A61K 9/5026; A61K 9/5031; A61K 9/5146; A61K 9/5153
See application file for complete search history.

(56) References Cited

U.S. PATENT DOCUMENTS

| | | |
|---|---|---|
| 4,857,602 A | 8/1989 | Casey |
| 4,994,074 A | 2/1991 | Bezwada |
| 4,997,652 A | 3/1991 | Wong |
| 5,013,556 A | 5/1991 | Woodle |
| 5,412,072 A | 5/1995 | Sakurai |
| 5,522,842 A | 6/1996 | Shalaby |
| 5,540,930 A | 7/1996 | Guy |
| 5,552,160 A | 9/1996 | Liversidge |
| 5,567,435 A | 10/1996 | Hubbell |
| 5,576,311 A | 11/1996 | Guy |
| 5,578,325 A | 11/1996 | Domb |
| 5,696,298 A | 12/1997 | Emanuele |
| 5,710,135 A | 1/1998 | Leenders |
| 5,869,130 A | 2/1999 | Ferrier |
| 5,932,462 A | 8/1999 | Harris |
| 6,007,845 A | 12/1999 | Domb |
| 6,235,869 B1 | 5/2001 | Roby |
| 6,270,806 B1 | 8/2001 | Liversidge |
| 6,287,588 B1 | 9/2001 | Shih |
| 6,413,539 B1 | 7/2002 | Shalaby |
| 6,432,381 B2 | 8/2002 | Liversidge |
| 6,495,164 B1 | 12/2002 | Ramstack |
| 6,589,549 B2 | 7/2003 | Shih |
| 6,706,289 B2 | 3/2004 | Lewis |
| 7,550,154 B2 | 6/2009 | Saltzman |
| 7,638,137 B2 | 12/2009 | Chauhan |
| 7,645,736 B2 | 1/2010 | Bender |
| 7,648,959 B2 | 1/2010 | Bender |
| 8,071,795 B2 | 12/2011 | VanMeir |
| 8,354,476 B2 | 1/2013 | Hanes |
| 8,394,799 B2 | 3/2013 | Lee |
| 8,409,607 B2 | 4/2013 | Hughes |
| 8,465,778 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,663,674 B2 | 3/2014 | Wen |
| 8,889,193 B2 | 11/2014 | McDonnell |
| 8,911,768 B2 | 12/2014 | Whitcup |
| 8,957,034 B2 | 2/2015 | Hanes |
| 8,962,577 B2 | 2/2015 | Hanes |
| 9,056,057 B2 | 6/2015 | Popov |
| 2002/0035264 A1 | 3/2002 | Kararli |
| 2003/0042137 A1 | 3/2003 | Mao |
| 2003/0118550 A1 | 6/2003 | Kabanov |
| 2004/0162580 A1 | 8/2004 | Hain |
| 2004/0209806 A1 | 10/2004 | Rothenberg |
| 2004/0209807 A1 | 10/2004 | Quay |
| 2004/0234611 A1 | 11/2004 | Ahlheim |
| 2004/0258763 A1 | 12/2004 | Bell |
| 2005/0009910 A1 | 1/2005 | Hughes |
| 2005/0070448 A1 | 3/2005 | Kupper |
| 2005/0149118 A1 | 7/2005 | Koyfman |
| 2005/0149119 A1 | 7/2005 | Koyfman |
| 2007/0071756 A1 | 3/2007 | Peyman |
| 2007/0087989 A1 | 4/2007 | Huang |
| 2007/0093461 A1 | 4/2007 | Shafiee |
| 2007/0111959 A1 | 5/2007 | Yockman |
| 2007/0141143 A1 | 6/2007 | Smithey |
| 2007/0149593 A1 | 6/2007 | Ghosh |
| 2007/0231360 A1 | 10/2007 | Peyman |
| 2007/0238654 A1 | 10/2007 | Deschatelets |
| 2007/0249536 A1 | 10/2007 | Ma |
| 2007/0292475 A1* | 12/2007 | Campbell ............ A61K 9/0048 424/428 |
| 2008/0086199 A1 | 4/2008 | Dave |
| 2008/0166411 A1 | 7/2008 | Shah |
| 2008/0166414 A1 | 7/2008 | Hanes |
| 2008/0268243 A1 | 10/2008 | Stopek |
| 2008/0287341 A1 | 11/2008 | Chen |
| 2008/0287990 A1 | 11/2008 | Smit |
| 2008/0305172 A1 | 12/2008 | Ahlheim |
| 2009/0011040 A1 | 1/2009 | Naash |
| 2009/0060979 A1 | 3/2009 | Bezwada |
| 2009/0087494 A1 | 4/2009 | Kompella |
| 2009/0138041 A1 | 5/2009 | Stopek |
| 2009/0203709 A1 | 8/2009 | Steinberg |
| 2009/0220572 A1 | 9/2009 | Deschatelets |
| 2009/0226531 A1 | 9/2009 | Lyons |
| 2009/0234375 A1 | 9/2009 | Simon |
| 2009/0247604 A1 | 10/2009 | Tang |
| 2009/0291919 A1 | 11/2009 | Kaushal |
| 2010/0034749 A1 | 2/2010 | Schulze |
| 2010/0063135 A1 | 3/2010 | Dande |
| 2010/0094340 A1 | 4/2010 | Stopek |
| 2010/0152831 A1 | 6/2010 | Guo |
| 2010/0209469 A1 | 8/2010 | Bezwada |
| 2010/0215580 A1 | 8/2010 | Hanes |
| 2010/0227905 A1 | 9/2010 | Kabra |
| 2011/0264139 A1 | 10/2011 | Hunter |
| 2012/0028910 A1 | 2/2012 | Combal |
| 2012/0041481 A1 | 2/2012 | Daniloff |
| 2012/0052041 A1 | 3/2012 | Basu |
| 2012/0121661 A1 | 5/2012 | Schwartz |
| 2012/0157499 A1 | 6/2012 | Hughes |
| 2012/0201873 A1 | 8/2012 | Hohlbaum |
| 2012/0245629 A1 | 9/2012 | Gross |
| 2012/0245829 A1 | 9/2012 | Viele |
| 2012/0269894 A1 | 10/2012 | Ahlheim |
| 2012/0288464 A1 | 11/2012 | Carmichael |
| 2012/0303010 A1 | 11/2012 | Vijfvinkel |
| 2013/0041407 A1 | 2/2013 | Montenegro |
| 2013/0071349 A1 | 3/2013 | Robinson |
| 2013/0122064 A1 | 5/2013 | Ahlheim |
| 2013/0164343 A1 | 6/2013 | Hanes |
| 2013/0183244 A1 | 7/2013 | Hanes |
| 2013/0217657 A1 | 8/2013 | Lindstrom |
| 2013/0226234 A1 | 8/2013 | Avelar |
| 2013/0236556 A1 | 9/2013 | Lai |
| 2013/0272994 A1 | 10/2013 | Fu |
| 2013/0274217 A1 | 10/2013 | Hanes |
| 2013/0316001 A1 | 11/2013 | Popov |
| 2013/0316006 A1 | 11/2013 | Popov |
| 2013/0316009 A1 | 11/2013 | Popov |

(56) References Cited

U.S. PATENT DOCUMENTS

| | | |
|---|---|---|
| 2013/0323313 A1 | 12/2013 | Suk |
| 2014/0031408 A1 | 1/2014 | Edelman |
| 2014/0107025 A1 | 4/2014 | Wirostko |
| 2014/0178475 A1 | 6/2014 | Figueiredo |
| 2014/0212661 A1 | 7/2014 | Khan |
| 2014/0248358 A1 | 9/2014 | Figueiredo |
| 2014/0249158 A1 | 9/2014 | Figueiredo |
| 2014/0276482 A1 | 9/2014 | Astafieva |
| 2014/0294986 A1 | 10/2014 | Liu |
| 2014/0329913 A1 | 11/2014 | Hanes |
| 2015/0044270 A1 | 2/2015 | McDonnell |
| 2015/0086484 A1 | 3/2015 | Hanes |
| 2015/0125539 A1 | 5/2015 | Popov |
| 2015/0265542 A1 | 9/2015 | Popov |
| 2015/0265543 A1 | 9/2015 | Popov |
| 2015/0297531 A1 | 10/2015 | Ensign |

FOREIGN PATENT DOCUMENTS

| | | |
|---|---|---|
| WO | 9901498 | 1/1999 |
| WO | 0046147 | 8/2000 |
| WO | 2002038127 | 5/2002 |
| WO | 2004060977 | 7/2004 |
| WO | 2005055985 | 6/2005 |
| WO | 2005072710 | 8/2005 |
| WO | 2006063249 | 6/2006 |
| WO | 2006109177 | 10/2006 |
| WO | 2006116107 | 11/2006 |
| WO | 2007016380 | 2/2007 |
| WO | 2007084418 | 7/2007 |
| WO | 2008030557 | 3/2008 |
| WO | 2010040188 | 4/2010 |
| WO | 2010132664 | 11/2010 |
| WO | 2011080148 | 7/2011 |
| WO | 2013110028 | 7/2013 |
| WO | 2013138343 | 9/2013 |
| WO | 2013138346 | 9/2013 |
| WO | 2013166385 | 11/2013 |
| WO | 2013166408 | 11/2013 |
| WO | 2013166436 | 11/2013 |
| WO | 2013166498 | 11/2013 |
| WO | 2014047439 | 3/2014 |

OTHER PUBLICATIONS

Cattel, et al., "From conventional to stealth liposomes a new frontier in cancer chemotherapy", Tumori, 83(3)237-49 (2003).

Garbuzenko, et al., "Effect of grafted PEG on liposome size and on compressibility and packing of lipid bilayer", Chem Phys Lipids, 135:117-29 (2005).

Immordino, et al., "Stealth liposomes: review of the basic science, rationale, and climical applications, existing and potential", Int J Naomed., 1(3)297-315 (2006).

Peeters, et al., "Can ultrasound solve the transport barrier of the neural retina", Pharma Res., 25(11)2657-65 (2008).

Vegra, et al., "Flurbiprofen loaded biodegradable nanoparticles for ophthalmic administration", J Pharma Sci., 95(11)2393-405 (2006).

Ludwig, The use of mucoadhesive polymers in ocular drug delivery, Adv Drug Deliv Rev., 57:1595-639 (2005).

Memon, et al., "Optimization of formulation parameters on ocular loteprednol etabonate nanosuspension by media milling method", Int J Pharmacrut. Biol. Arch., 4:46-51 (2012).

Sahib, et al., "Solubilization of beclomethasone dipropionate in sterically stabilized phospholipid nanomicelles (SSMs):physicochemical and in vitro evaluations", Drug Des Dev Ther., 6:29-42 (2012).

Yang, et al., "Production of virus-mimetic mucus-penetrating particles for drug and gene delivery in mucosal tissues", Annual Meeting of AICHE Science and Engineering Forum, Nov. 16-21, Abstract 705B (2008).

Erdmann and Uhrich, "Synthesis and degradation characteristics of salicylic acid-derived poly(anhydride-esters)", Biomaterials, 21:1941-6 (2000).

Grisanti and Ziemssen, "Bevacizumab: Off-label uses in ophthalmology", Indian J Ophtalmol., 55(6):417-20 (2007).

Sagong, et al., "Intravitreal becacizumab for the treatment of neovascular glaucoma associated with central retinal artery occlusion", Koren J Ophthalmol., 23:215-8 (2009).

Jain and Kumar, "Self assembly of amphiphiiic (PEG)(3)-PLA copolymer as polymersomes: preparation, characterization, and their evaluation as drug carrier": Biomacromaolecules, 11:1027-35 (2010).

Desai, "Pluronic F127-based ocular delivery system containing biodegradable polyisobutylcyanoacrylate nanocapules of pilocarpine", Drug Delivery, 7:201-7 (2000).

Aich, et al., "Development of delivery methods for carbohydrate-based drugs: controlled release of biologically-active short chain fatty-acid-hexosamine analogs", Glycoconj. J., 27(4):445-59 (2010).

Ben-Shabat, S. et al., PEG-PLA block copolymer as potential drug carrier; preparation and characterization; Macromol. Biosci. 6:1019-1025 (2006).

Deosarkar, et al., "Polymeric particles conjugated with a ligand to VCAM-1 exhibit selective, avid, and focal adhesion to sites of atherosclerosis", Biotech. Bioeng., 101(2):400-7 (2008).

Dong, et al., "Vascular cell-adhesion molecule-1 plays a central role in he proangiogenic effects of oxidative stress", PNAS, 108(35):14614-9 (2011).

Escobar-Chavez, "Application of thermo-reversible pluronic F-127 gets in pharmaceutical formulations", J Pharma Sci., 9(3):339-58 (2006).

Fiegel, et al., "Poly(ether-anhydride) dry powder aerosols for sustained drug delivery in the lungs", J Control Release, 96:411-23 (2004).

Govender, et al., "PLGA nanoparticles prepared by nanoprecipitation: drug loading and release studies of a water soluble drug", J Cont. Rel., 57:171-85 (1999).

Kompella, et al., "Luteinizing hormone-releasing homone agonist and transferrin functionalizations enhance nanoparticle delivery in a novel bovine ex vivo eye model", Mol. Vis., 12:1185-98 (2006).

Newman, et al., "Uptake of poly(D,L-lactic-co-glycolic-acid) microspheres by antigen-presenting cells in vivo", J Biomed Mater Res., 80(3):480-6 (2002).

Okamoto, et al., Transgenic mice with increased expression of vascular endothelial growth factor in the retina: a new model of intraretinal and subretinal neovascularization, Am. J. Pathol, 151:281-291 (1997).

Saishin, et al., "VEGF-TRAP(R1R2) suppresses choroidal neovascularization and VEGF-induced breakdown of the blood-retinal barrier", J. Cell Physiol., 195:241-8 (2003).

Singh, et al., "Cationic microparticles: A potent delivery system for DNA vaccines", PNAS, 98(2):811-6 (2000).

Smith, et al., Oxygen-induced retinopathy in the mouse, Invest. Ophthalmol. Vis. Sci. 35:101-111 (1994).

Sobczak, et al., "Synthesis and characterization of polyester conjugates of ciprofloxacin", Eu. J. Med Chem., 45(9):3844-9 (2010).

Tanaka, et al., "Development of cell-penetrating peptide-modified MPEG-PCL diblock copolymeric nanoparticles for systemic gene delivery", Intl J Pharmac, 398:(1-2):229-38 (2010).

Tang, et al., "Enhanced efficacy of local etoposide delivery by poly(ether-anhydride)particles against small cell lung cancer in vivo", Biomaterials, 31:339-44 (2010).

Tobe, et al., "Targeted disruption of the FGF2 gene does not prevent choroidal neovascularization in a murine model", Am. J. Pathol. 153:1641-1646 (1998).

Yokoyama, et al., "Characterization and anticancer activity of the micelle-forming polymeric anticancer drug adriamycin-conjugated poly(ethylene glycol)-poly(aspartic acid) block copolymer", Cancer Res., 60:1693-1700 (1990).

Yoshida, et al., Digoxin inhibits retinal ischemia-induced HIF-1alpha expression and ocular neovascularization, FASEB J. 24:1759-1767 (2010).

Bourges, et al., "Pcular drug delivery targeting the retina and retinal pigment epithelium using polyactide nanoparticles", Inv Ophthalmology Vis Sci., 44(8):3562-9 (2003).

(56) References Cited

OTHER PUBLICATIONS de Kozak, et al., "Intraocular injection of tamoxifen-loaded nanoparticles: a new treatment of experimental autoimmune uveoeretinitis", Eur. J Immunol., 34:3702-12 (2004).
Giannavola, et al., "Influence of preparation conditions of Acyclovir-loaded poly-d, l-lactic acid nanospheres and effect of PEG coating of ocular drug bioavailability", Pharma. Res., 20(4):584-90 (2003).
Lai, et al., "Rapid transport of large polymeric nanoparticles in fresh undiluted human mucus", PNAS, 104(5):1482-7 (2007).
Soppimath, et al., "Biodegradable polymeric nanoparticles as drug delivery devise", J Cont. Release, 70:1-20 (2001).
Suh, et al., "PEGylation nanoparticles improves their cytoplasmic transport", Int. J Nanomed., 2(4):735-41 (2007).
Veronese, et al., "PEG-doxorubicin conjugates: influence of polymer structure on drug release in vitro cytotoxicity, biodistribution, and antitumor activity", Bioconjig Chem., 16(4):776-84 (2005).

* cited by examiner

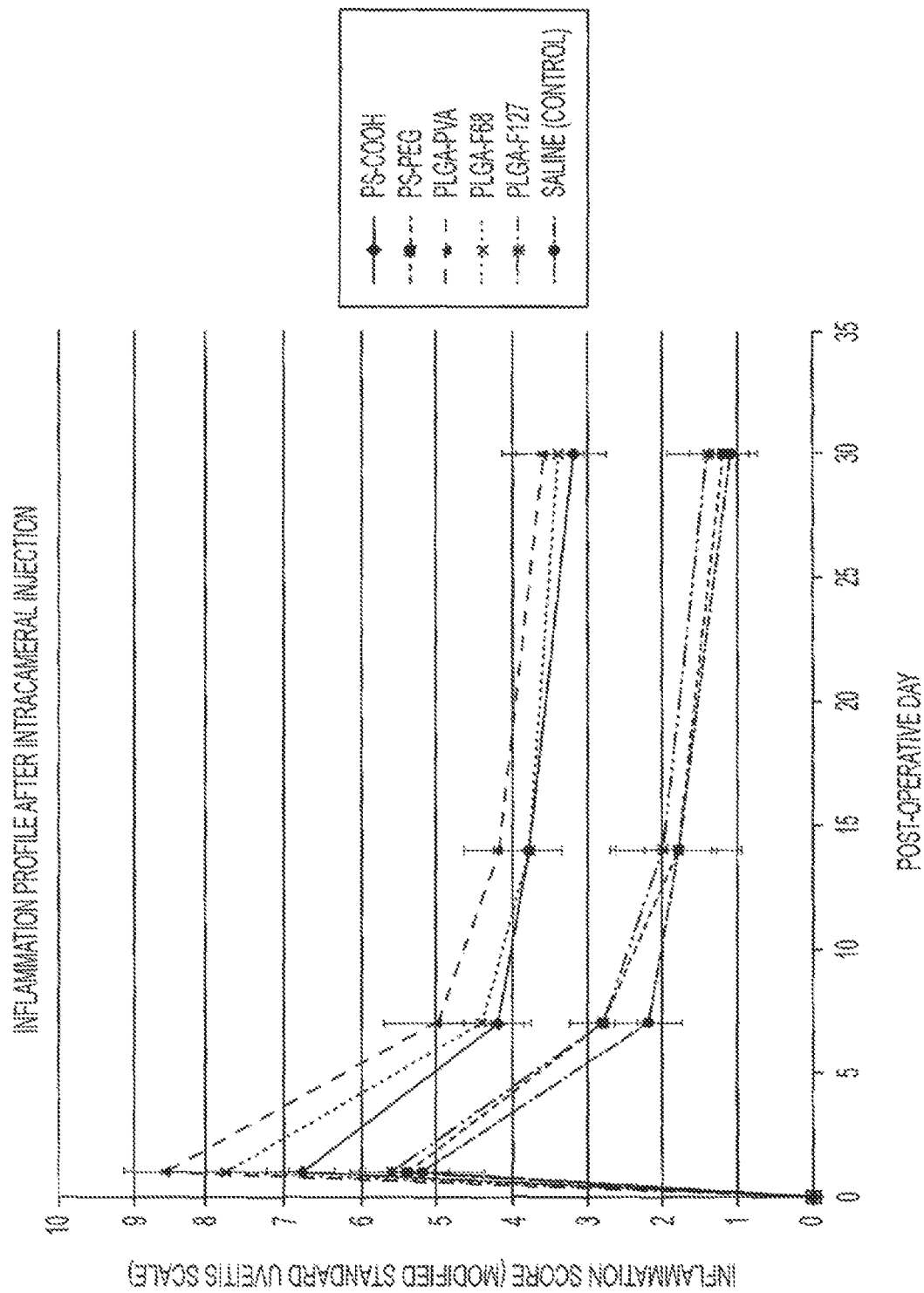

SUSTAINED DELIVERY OF THERAPEUTIC AGENTS TO AN EYE COMPARTMENT

CROSS REFERENCE TO RELATED APPLICATIONS

This application is a continuation of U.S. application Ser. No. 14/521,904, filed Oct. 23, 2014, entitled "Sustained Delivery of Therapeutic Agents to an Eye Compartment", by Peter J. McDonnell, Yasin A. Khan, Samuel K. Lai, Renata T. Kashiwabuchi, Ashley Behrens, and Justin S. Hanes, which is a continuation of U.S. application Ser. No. 13/581,454, filed on Aug. 27, 2012, which is a National Stage of International Application No. PCT/US2011/026321 filed with the Patent Cooperation Treaty on Feb. 25, 2011, which claims priority to and benefit of U.S. Provisional Applications Nos. 61/308,053, 61/308,042, and 61/308,035, both filed on Feb. 25, 2010, the contents of each being hereby incorporated by reference in their entirety.

TECHNICAL FIELD

The compositions and methods disclosed herein can be used for treating eye disorders, for example by administering a drug delivery system into an eye compartment of a patient.

BACKGROUND

Treatment of eye disorders can pose significant problems. For example, the management of many corneal diseases requires that therapeutic agents, such as drugs or other medications, remain at therapeutic levels in the corneal tissue for extended periods of time. Topical drops remain the most common route of drug administration to the eye, especially the cornea. Certain patients, however, including those patients having fungal and/or amoebic infections of the cornea, as well as corneal transplant recipients, require therapeutic doses of medications to be continuously maintained in the corneal tissues. To achieve such therapeutic doses of a particular medication in corneal tissues, such patients are required to endure lengthy and arduous dosing regimens that often involve topically instilling medications hourly.

The efficacy of topical dosing can be diminished by poor patient compliance. The repeated administration of one or more medications can also lead to toxicity, which can be related to excess dosing of the medications and/or their preservative agents. Injections of free-standing medications into the corneal stroma also have been employed in certain situations. This approach, however, fails to result in sustained presence of medications within the therapeutic window due to rapid diffusion of the medication out of the cornea. The combination of poor compliance and poor penetration of topically-administered medications into the corneal stroma can result in treatment failure, even when the pathogenic organism or other cause of disease is known to be "sensitive" to the therapy or should otherwise respond to the medication being applied to the eye.

Such treatment difficulties are not only observed with corneal diseases. Disorders common to the anterior chamber (AC) can also pose problems. For example, cataract extraction is one of the most commonly performed surgical procedures in the United States. Both the incidence of cataracts and the frequency of their extraction surgeries continue to rise. Anti-inflammatory agents and antimicrobials both are required during the post-operative period and typically must be administered for many weeks. Unfortunately, the poor ocular bioavailability of these drugs often necessitates complicated and arduous dosing regimens that can lead to poor patient compliance, which, in turn, ultimately contributes to poor surgical outcomes and other complications. Current state-of-the art treatment involves sustained delivery systems that are injected into the subconjunctival space at the end of surgery. However, such sustained release drug systems afford limited intraocular bioavailability of delivered medications due to barriers to drug penetration. Further, medications delivered to an extraocular site, even in a sustained manner, will have lower intraocular bioavailability due to barriers that prevent penetration.

Injecting medications directly into the AC of the eye at the end of surgery has been an alternative to topical treatment. Free-standing medications injected into the AC, however, are readily eliminated during aqueous humor clearance. As a result, the retention of medications injected into the AC is short and their bioavailability fails to meet clinical guidelines.

The delivery of medications to the posterior segment of the eye has also been a challenge for ophthalmologists. Currently, the successful management of many retinal diseases often requires multiple intravitreal injections of medication per year. Retinal diseases, such as diabetic retinopathy and age-related macular degeneration, among others, continue to represent major causes of irreversible vision loss in the United States. The treatment of these conditions is complicated by the difficulty of delivering medications to the retina. The direct delivery of drugs to the vitreous chamber has become an important tool in the arsenal of retinal disease management.

Unfortunately, the chronic and progressive nature of many retinal diseases necessitates repeated injections to provide continued treatment. The current regimens, which vary based on the disease, its stage, and the medications used, can include up to six intraocular injections per year. Each intravitreal injection, however, is associated with the risk of developing serious and vision-threatening infections and even traumatic retinal injury.

SUMMARY

In one aspect, the invention provides methods for treating eye disorders in a patient in need thereof. The methods can include, for example, administering a drug delivery system into an eye compartment of the patient, the drug delivery system having (i) a particle including a core; (ii) a coating associated with the particle, wherein the coating is covalently or non-covalently associated with the particle and presents a hydrophilic region to the environment around the particle; and (iii) a therapeutically effective amount of a therapeutic agent, thereby treating the eye disorder. In some embodiments, the eye compartment exhibits reduced inflammation or IOP than if a drug delivery system using an uncoated particle were administered to the patient. The inflammation or IOP can be reduced by, for example, at least about 10%, or at least about 30%, or at least about 50%. In some embodiments, the core includes a biocompatible polymer.

In some embodiments, the coating includes one or more molecules having hydrophilic regions and hydrophobic regions. For example, at least about 50% of the hydrophobic regions in the coating molecules have a molecular mass of least about 2 kDa, or at least about 3 kDa. The hydrophobic regions can include, for example, PPO. The hydrophilic regions can include, for example, PEG. The particles can have a diameter of, for example, less than about 100,000 nm, or less than about 50,000 nm, or less than about 10,000 nm, or less than about 5,000 nm, or less than about 1,000 nm. In some embodiments, the particle has a diameter of about 200 nm.

The particle can include, for example, a biodegradable polymer such as poly(lactic-co-glycolic acid). The coating can be, for example, bound covalently to the particle, or it can be non-covalently associated with the particle. In some embodiments, the coating includes one or more of Pluronic P103, Pluronic P105, and poloxamer 407.

In some embodiments, administering the drug delivery system involves injecting the drug delivery system into an eye compartment, such as the vitreous chamber, the sclera, the stroma or the anterior chamber. The drug delivery system can include a therapeutic agent such as one or more of an anti-inflammatory drug, an antimicrobial agent, an anti-angiogenesis agent, an immunosuppressant, an antibody, an antibody fragment, a steroid, a chemotherapeutic agent, an ocular anti-hypertensive drug and combinations thereof. In some embodiments, the drug delivery system provides sustained release of the therapeutic agent over a period of time, for example at least about 1 day, or at least about 1 week, or at least about 4 weeks.

In another aspect, the invention provides drug delivery systems. The drug delivery system can include: (i) a particle including a core; (ii) a coating associated with the particle, wherein the coating is covalently or non-covalently associated with the particle and presents a hydrophilic region to the environment around the particle; and (iii) a therapeutically effective amount of a therapeutic agent. The drug delivery system can be suitable for administration into an eye compartment, such as the vitreous chamber, the sclera, the corneal stroma and the anterior chamber. The core can include, for example, a biocompatible polymer. In some embodiments, the drug delivery system brings about reduced inflammation or IOP when administered to the patient than if a drug delivery system using an uncoated particle were administered to the patient, for example by at least about 10%, or at least about 30%, or at least about 50%. In some embodiments, the coating includes one or more molecules having hydrophilic regions and hydrophobic regions. For example, at least about 50% of the hydrophobic regions in the coating molecules have a molecular mass of at least about 2 kDa, or at least about 3 kDa. In some embodiments, the hydrophobic regions comprise PPO. In some embodiments, the hydrophilic regions comprise PEG. The particle can include, for example, a biodegradable polymer such as poly(lactic-co-glycolic acid). The coating can include, for example, one or more of Pluronic P103, Pluronic P105 and poloxamer 407. The particles can have a diameter of, for example, less than about 100,000 nm, or less than about 50,000 nm, or less than about 10,000 nm, or less than about 5,000 nm, or less than about 1,000 nm. In some embodiments, the particle has a diameter of about 200 nm. In some embodiments, the therapeutic agent is one or more of an anti-inflammatory drug, an antimicrobial agent, an anti-angiogenesis agent, an immunosuppressant, an antibody, an antibody fragment, a steroid, a chemotherapeutic agent, an ocular anti-hypertensive drug and combinations thereof. The drug delivery system can be suitable for administration into the eye compartment by injection.

The drug delivery system can also include, for example, (i) a substrate; (ii) a coating associated with the substrate, wherein the coating presents a hydrophilic region to the environment around the substrate; and (iii) a therapeutically effective amount of a therapeutic agent. The drug delivery system can, for example, bring about reduced inflammation when administered to the patient than if a drug delivery system comprising an uncoated substrate were administered to the patient.

BRIEF DESCRIPTION OF THE DRAWINGS

FIG. 1 is a graph depicting the inflammation profile in female New Zealand white rabbits after intracameral injection of several particle-coating combinations according to the compositions and methods disclosed herein.

DETAILED DESCRIPTION

The presently disclosed subject matter may be embodied in many different forms and should not be construed as limited to the embodiments set forth herein. Indeed, many modifications and other embodiments of the presently disclosed subject matter will come to mind for one skilled in the art to which the presently disclosed subject matter pertains having the benefit of the teachings presented in the descriptions included herein. Therefore, it is to be understood that the presently disclosed subject matter is not to be limited to the specific embodiments disclosed and that modifications and other embodiments are intended to be included within the scope of the disclosed subject matter.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes one or a plurality of subjects, unless the context clearly is to the contrary (e.g., a plurality of subjects), and so forth.

Throughout the specification and claim(s), the terms "comprising," "having," "including," or "containing" and any grammatical derivations thereof, are intended to be non-limiting, i.e., they are inclusive or open-ended, such that recitation of particular elements in a list does not exclude other like, but unrecited, elements that can be substituted or added to the recited elements.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100%; in some embodiments, ±50%; in some embodiments, ±20%; in some embodiments, ±10%; in some embodiments, ±5%; in some embodiments, ±1%; in some embodiments, ±0.5%; and in some embodiments, ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

In one aspect, methods for treating one or more eye disorders are disclosed. The methods can involve, for example, administering a drug delivery system into an eye compartment of a patient. In some embodiments, the drug delivery system can include: i) a particle containing a core; ii) a coating disposed on the surface of the particle, wherein the coating molecules have hydrophilic regions; and iii) a therapeutic agent, for example a therapeutically effective amount of a therapeutic agent. The coating molecules can include, for example, hydrophobic regions. In some embodiments, at least about 50% of the hydrophobic regions in the coating molecules have a molecular mass of least about 2 kDa. In some embodiments, the drug delivery system can include a particle and a coating; and in some embodiments, a particle, coating and therapeutic agent. The drug delivery system can contain, for example, a pharmaceutically acceptable carrier. The drug delivery system can be suitable for administration into an eye compartment of a patient, for example by injection into the eye compartment. In some embodiments, the core includes a biocompatible polymer. As used herein, unless the context indicates otherwise, "drug delivery system" and "particle composition" can be used interchangeably.

The particle in the drug delivery system can be of various sizes. The appropriate particle size can vary based on the method of administration, the eye compartment to which the drug delivery system is administered, the therapeutic agent employed and the eye disorder to be treated, as will be appreciated by a person of skill in the art in light of the teachings disclosed herein. For example, in some embodiments the particle has a diameter of at least about 1 nm, or from about 1 nm to about 50 microns. The particle can also have a diameter of, for example, from about 1 nm to about 30 microns; or from about 1 nm to about 10 microns; or from about 1 nm to about 6 microns; from about 1 nm to about 5 microns; or from about 1 nm to about 3 microns; or from about 1 nm to about 1000 nm; or from about 25 nm to about 750 nm; or from about 50 nm to about 500 nm; or from about 100 nm to about 300 nm. In some embodiments, the average particle size can be about 1 nm, about 10 nm, about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm, or about 2,000 nm, or about 5,000 nm, or about 6,000 nm, or about 10,000 nm, or about 20,000 nm, or about 50,000 nm, or about 100,000 nm. In some embodiments, the particle size can be about 100 microns or less, about 50 microns or less, about 30 microns or less, about 10 microns or less, about 6 microns or less, about 5 microns or less, about 3 microns or less, about 1000 nm or less, about 800 nm or less, about 600 nm or less, about 500 nm or less, about 400 nm or less, about 300 nm or less, about 200 nm or less, or about 100 nm or less. In some embodiments, the particle can be a nanoparticle or a microparticle, as these terms are defined herein. In some embodiments, the drug delivery system can contain a plurality of particles. The particles can be all nanoparticles, all microparticles, or a combination of nanoparticles and microparticles.

In some embodiments, the drug delivery system includes a particle comprising a core. The core can be, for example, a small molecule, a polymer, a lipid, a protein, a carbohydrate, a viral carrier, a virosome, a sterol, a liposome, a metal, a metal oxide (e.g., silica), a quantum dot, a therapeutic agent in pure or substantially pure form (e.g., in crystal form), and the like, as well as any combination of any of the foregoing. The particle can include, without limitation, one or more lipid-based drug carriers.

The particles of the drug delivery system can include a biocompatible polymer. As used herein, the term "biocompatible polymer" encompasses any polymer that can be administered to a patient without adverse effects to the patient, or for which any adverse effects are deemed by a person having ordinary skill in the art to be outweighed by the benefits brought about by the drug delivery system in light of the mode of administration, the therapeutic agent employed, and/or the eye disorder to be treated, and also when considered in light of the availability of alternative therapeutic regimen and their characteristics.

Examples of biocompatible polymers include but are not limited to polystyrenes; poly(hydroxy acid); poly(lactic acid); poly(glycolic acid); poly(lactic acid-co-glycolic acid); poly(lactic-co-glycolic acid); poly(lactide); poly(glycolide); poly(lactide-co-glycolide); polyanhydrides; polyorthoesters; polyamides; polycarbonates; polyalkylenes; polyethylenes; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; poly(vinyl chloride); polyvinylpyrrolidone; polysiloxanes; poly(vinyl alcohols); poly(vinyl acetate); polyurethanes; copolymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly (ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); hydroxyethyl methacrylate (HEMA); copolymers of HEMA with acrylate; copolymers of HEMA with polymethylmethacrylate (PMMA); polyvinylpyrrolidone/vinyl acetate copolymer (PVP/VA); acrylate polymers/copolymers; acrylate/carboxyl polymers; acrylate hydroxyl and/or carboxyl copolymers; polycarbonate-urethane polymers; silicone-urethane polymers; epoxy polymers; cellulose nitrates; polytetramethylene ether glycol urethane; polymethylmethacrylate-2-hydroxyethylmethacrylate copolymer; polyethylmethacrylate-2-hydroxyethylmethacrylate copolymer; polypropylmethacrylate-2-hydroxyethylmethacrylate copolymer; polybutylmethacrylate-2-hydroxyethylmethacrylate copolymer; polymethylacrylate-2-hydroxyethylmethacrylate copolymer; polyethylacrylate-2-hydroxyethylmethacrylate copolymer; polypropylacrylate-2-hydroxymethacrylate copolymer; polybutylacrylate-2-hydroxyethylmethacrylate copolymer; copolymermethylvinylether maleicanhydride copolymer; poly (2-hydroxyethyl methacrylate) acrylate polymer/copolymer; acrylate carboxyl and/or hydroxyl copolymer; olefin acrylic acid copolymer, ethylene acrylic acid copolymer; polyamide polymers/copolymers; polyimide polymers/copolymers; ethylene vinylacetate copolymer; polycarbonate urethane; silicone urethane; polyvinylpyridine copolymers; polyether sulfones; polygalactin, poly-(isobutyl cyanoacrylate), and poly(2-hydroxyethyl-L-glutamine); polydimethyl siloxane; poly(caprolactones); poly(ortho esters); polyamines; polyethers; polyesters; polycarbamates; polyureas; polyimides; polysulfones; polyacetylenes; polyetheneimines; polyisocyanates; polyacrylates; polymethacrylates; polyacrylonitriles; polyarylates; and combinations, copolymers and/or mixtures of two or more of any of the foregoing. In some cases, the particle includes a hydrophobic material and at least one bioactive agent. In certain embodiments, the hydrophobic material is used instead of a polymer. In other embodiments, the hydrophobic material is used in addition to a polymer.

In some embodiments, the presently disclosed particles contain a biodegradable polymer. The biodegradable polymer can contain a synthetic polymer, although natural polymers also can be used. The polymer can be, for example, poly(lactic-co-glycolic acid) (PLGA), polystyrene or combinations thereof. The polystyrene can, for example, be modified with carboxyl groups. Other examples of biodegradable polymers include poly(hydroxy acid); poly(lactic acid); poly(glycolic acid); poly(lactic acid-co-glycolic acid); poly(lactide); poly(glycolide); poly(lactide-co-glycolide); polyanhydrides; polyorthoesters; polyamides; polycarbonates; polyalkylenes; polyethylene; polypropylene; polyalkylene glycols; poly(ethylene glycol); polyalkylene oxides; poly(ethylene oxides); polyalkylene terephthalates; poly (ethylene terephthalate); polyvinyl alcohols; polyvinyl ethers; polyvinyl esters; polyvinyl halides; poly(vinyl chloride); polyvinylpyrrolidone; polysiloxanes; poly(vinyl alcohols); poly(vinyl acetate); polyurethanes; co-polymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly (hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly (lactide-co-caprolactone); blends of poly(lactide-co-caprolactone); polygalactin; poly-(isobutyl cyanoacrylate); poly (2-hydroxyethyl-L-glutam-nine); and combinations, copolymers and/or mixtures of one or more of any of the foregoing. Furthermore, as a person of ordinary skill in the art would appreciate, some of the polymers listed above as "biocompatible" can also be considered biodegradable, whether or not they are included in the above listing of representative biodegradable polymers. As used herein, "derivatives" include polymers having substitutions, additions of chemical groups and other modifications routinely made by those skilled in the art.

In some embodiments, the drug delivery systems contain a particle with a coating on the surface, wherein the coating molecules have hydrophilic regions and, optionally, hydrophobic regions, wherein the coated particle causes less inflammation than a similar, but uncoated particle, as measured by standard protocols, for example upon injection into the anterior chamber of a New Zealand white rabbit or a human.

The drug delivery system can also include a coating. The coating can be disposed on the surface of the particle, for example by bonding, adsorption or by complexation. The coating can also be intermingled or dispersed within the particle as well as disposed on the surface of the particle.

The coating can be, for example, polyethylene glycol, polyvinyl alcohol (PVA), or similar substances. The coating can be, for example, vitamin E-PEG 1 k or vitamin E-PEG 5 k or the like. Vitamin E-PEG 5 k can help present a dense coating of PEG on the surface of a particle. The coating can also include nonionic surfactants such as those composed of polyaklyene oxides, e.g., polyoxyethylene (PEO), also referred to herein as polyethylene glycol; or polyoxypropylene (PPO), also referred to herein as polypropylene glycol (PPG), and can include co-polymers of more than one alkylene oxide. The copolymers can be, for example, random copolymers, block copolymers or graft copolymers. In some embodiments, the coating includes a polyoxyethylene-polyoxypropylene copolymer, e.g., block copolymers of ethylene oxide and propylene oxide. (i.e., poloxamers). Examples of poloxamers suitable for use in the coatings include, for example, poloxamers 188, 237, 338 and 407. These poloxamers are available under the trade name Pluronic® (available from BASF, Mount Olive, N.J.) and correspond to Pluronic®-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about $E_{101} P_{56} E_{101}$ to about $E_{106} P_{70} E_{106}$, or about $E_{106} P_{56} E_{101}$, or about $E_{106} P_{70} E_{106}$, with an average molecular mass of about 10,000 to about 15,000 Da, or about 12,000 to about 14,000 Da, or about 12,000 to about 13,000 Da, or about 12,600 Da. For example, the NF forms of poloxamers or Pluronic® polymers can be used.

In some embodiments, the coating can be, for example Pluronic® P103 or Pluronic® P105. Pluronic® P103 is a block copolymer with an average molecular mass of about 3,000 Da to about 6,000 Da, or about 4,000 Da to about 6,000 Da, or about 4,950 Da. Pluronic® P105 is a block copolymer with an average molecular mass of about 5,000 Da to about 8,000 Da, or about 6,000 Da to about 7,000 Da, or about 6,500 Da.

In some embodiments, the coating can have an average molecular weight of about 9,000 Da or greater, about 10,000

Da or greater, about 11,000 Da or greater or about 12,000 Da or greater. In exemplary embodiments, the coating can have an average molecular weight of from about 10,000 to about 15,000 Da, or about 12,000 to about 14,000 Da, or about 12,000 to about 13,000 Da, or about 12,600 Da. In some embodiments, the coating can be selected from Pluronic® P103, P105, F-68, F-87, F-108 and F-127, from Pluronic® P103, P105, F-87, F-108 and F-127, or from Pluronic® P103, P105, F-108 and F-127, or from Pluronic® P103, P105 and F-127. In some embodiments, the coating can be Pluronic® F-127. In representative embodiments, the coating is associated with the particles. For example, the coating can be covalently attached to the particles. In representative embodiments, the coating is polyethylene glycol, which is covalently attached to the particle, yielding what is commonly referred to as a PEGylated particle.

In some embodiments, the coating is non-covalently associated with the particle. This association can be held together by any force or mechanism of molecular interaction that permits two substances to remain in substantially the same positions relative to each other, including intermolecular forces, dipole-dipole interactions, van der Waals forces, hydrophobic interactions, electrostatic interactions and the like. In some embodiments, the coating is adsorbed onto the particle. According to representative embodiments, a non-covalently bound coating can be comprised of portions or segments that promote association with the particle, for example by electrostatic or van der Waals forces. In some embodiments, the interaction is between a hydrophobic portion of the coating and the particle. Embodiments include particle coating combinations which, however attached to the particle, present a hydrophilic region, e.g. a PEG rich region, to the environment around the particle coating combination. The particle coating combination can provide both a hydrophilic surface and an uncharged or substantially neutrally-charged surface, which can be biologically inert.

Suitable coatings for use according to the compositions and methods disclosed herein can be made up of molecules having hydrophobic regions as well as hydrophilic regions. Without wishing to be bound by any particular theory, it is believed that the hydrophobic regions of the coating molecules are able to form adsorptive interactions with the surface of the particle, and thus maintain a non-covalent association with it, while the hydrophilic regions orient toward the surrounding, frequently aqueous, environment. In some embodiments the hydrophilic regions are characterized in that they avoid or minimize adhesive interactions with substances in the surrounding environment. Suitable hydrophobic regions in the coatings can include, for example, PPO, vitamin E and the like, either alone or in combination with each other or with other substances. Suitable hydrophilic regions in the coatings can include, for example, PEG, heparin, polymers that form hydrogels and the like, alone or in combination with each other or with other substances.

Representative coatings according to the compositions and methods disclosed herein can include molecules having, for example, hydrophobic segments such as PPO segments with molecular weights of at least about 1.8 kDa, or at least about 2 kDa, or at least about 2.5 kDa, or at least about 3 kDa, or at least about 3.5 kDa, or at least about 4.0 kDa, or at least about 4.5 kDa, or at least about 5.0 kDa or more. In some embodiments, the coatings can have PPO segments with molecular weights of from about from about 1.8 kDa to about 10 kDa, or from about 2 kDa to about 5 kDa, or from about 2.5 kDa to about 4.5 kDa, or from about 2.5 kDa to about 3.5 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges. In some embodiments, the coatings are biologically inert. Compounds that generate both a hydrophilic surface and an uncharged or substantially neutrally-charged surface can be biologically inert.

In some embodiments, the coating can include, for example, one or more of the following: anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin), mucolytic agents, N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, dornase alfa, neltenexine, erdosteine, various DNases including rhDNase, agar, agarose, alginic acid, amylopectin, amylose, beta-glucan, callose, carrageenan, cellodextrins, cellulin, cellulose, chitin, chitosan, chrysolaminarin, curdlan, cyclodextrin, dextrin, ficoll, fructan, fucoidan, galactomannan, gellan gum, glucan, glucomannan, glycocalyx, glycogen, hemicellulose, hydroxyethyl starch, kefiran, laminarin, mucilage, glycosaminoglycan, natural gum, paramylon, pectin, polysaccharide peptide, schizophyllan, sialyl lewis x, starch, starch gelatinization, sugammadex, xanthan gum, xyloglucan, L-phosphatidylcholine (PC), 1,2-dipalmitoyl-phosphatidycholine (DPPC), oleic acid, sorbitan triolcate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, polyoxyethylene (4) lauryl other, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, sunflower seed oil, lecithin, oleic acid, sorbitan trioleate, and combinations of two or more of any of the foregoing.

The particle-coating combinations can be made up of any combination of particle and coating substances disclosed or suggested herein. Examples of such combinations include, for example, polystyrene-PEG, or PLGA-Pluronic® F-127.

In some embodiments, the coating is associated with the particle, either through covalent or non-covalent interactions with the particle. Coatings that can be covalently bound to the particle include, for example, PEG. PEG can be covalently bound to any suitable polymer that can be included in the particle. An example of a polymer that can be coated with PEG is polystyrene. Other particles that can be PEGylated are known in the art.

The drug delivery system can include one or more therapeutic agents. Any therapeutic agent can be used which is suitable to administration in the drug delivery system disclosed herein, as would be appreciated by a person of ordinary skill. Examples of types of such therapeutic agents include anti-inflammatory drugs, antimicrobial agents, anti-angiogenesis agents, immunosuppressants, antibodies, steroids, chemotherapeutic agents, ocular anti-hypertensive drugs and combinations thereof. Examples of therapeutic agents that can be used the drug delivery system disclosed herein include acyclovir, amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEOF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometurone, rimexolone, anecortave, cyclosporine, methotrexate, tacrolimus and combinations thereof.

The drug delivery systems disclosed herein, which can include one or more therapeutic agents, can be used to treat eye disorders according to the methods disclosed herein. The drug delivery system can be used to treat any eye disorder that, in the judgment of a person of ordinary skill in the art, would be effectively treated with any of the drug delivery systems disclosed herein. Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

According to the methods disclosed herein, the drug delivery system can be administered into an eye compartment of a patient with an eye disorder. The drug delivery system can be administered to any eye compartment that is susceptible to an eye disorder treatable with the compositions and methods disclosed herein. Examples of such eye compartments include the vitreous chamber, subretinal space, subchoroidal space, the episclera, the conjunctiva, the sclera, the anterior chamber, and the cornea and compartments therein (e.g., subepithelial, intrastromal, endothelial).

The drug delivery system can be administered via any route which is effective to deliver an effective amount of the therapeutic agent to the eye compartment to be treated. For example, the drug delivery system can be injected into the eye compartment to be treated, such as, for example, the vitreous chamber, subretinal space, subchoroidal space, the episclera, the conjunctiva, the sclera or the anterior chamber, and the cornea and compartments therein (e.g., subepithelial, intrastromal, endothelial).

The drug delivery systems disclosed herein provide sustained release of a therapeutic agent over a period of time. For example, after administration of the drug delivery system, the therapeutic agent can be released for at least about 6 hours, at least about 12 hours, at least about 1 day, at least about 2 days, at least about 3 days, at least about one week, at least about 2 weeks, at least about 3 weeks, at least about 4 weeks, at least about 5 weeks, at least about 6 weeks, at least about 7 weeks, at least about 2 months, at least about 3 months, at least about 6 months, at least about 9 months, at least about 1 year or more. Furthermore, according to the compositions and methods disclosed herein, administration of the drug delivery systems to the patient causes less inflammation or IOP over time than if other drug delivery systems are administered. Notwithstanding the foregoing, there may be some initial inflammation shortly after administration, even with the drug delivery system disclosed herein. However, a reduction of inflammation or IOP can be observed after about 2 days post-administration, or after about 5 days post-administration. Inflammation or IOP is reduced over time, even with administration of conventional or previously available drug delivery systems. However, the reduction or avoidance of inflammation or IOP when using methods and compositions disclosed herein is persistent and can continue to be observed for up to 30 days, up to 20 days, up to 15 days, or up to 10 days post-administration. The reduction or avoidance of inflammation or IOP can continue for at least about 10 days, at least about 15 days, at least about 20 days, or at least about 30 days post-administration.

In some embodiments, the drug delivery systems disclosed herein when administered to the vitreous chamber, the sclera, the anterior chamber or other eye compartment of a patient, achieve reduced or decreased inflammation, and thus, for example, reduced intraocular pressure (IOP) over that which would be brought about if, for example, an uncoated polymer particle, for example a particle otherwise similar to the coated particle, were administered to same eye compartment in the patient. Furthermore, drug delivery systems including particles and coatings according to the compositions and methods disclosed herein can reduce or avoid an increase in IOP over that which would be observed if uncoated particles of similar size were administered. Accordingly, the particle size threshold for inducing or increasing IOP can be higher for coated particles than it would be for uncoated particles. As a result, it may be possible to use larger particles for administration into an eye compartment, for example into the AC, if such particles are coated according to the compositions and methods disclosed herein. In some embodiments, the drug delivery systems disclosed herein provide the advantage of avoiding or reducing aggregation of particles after administration.

Inflammation and LOP can be measured after administration of the compositions disclosed herein by methods known in the art. For example, a Reichert Tono-Pen contact tonometer can be used to assess the IOP, and changes in IOP, in any eye compartment disclosed herein, for example the AC. The subjects, for example animals, can be evaluated on several post-injection days, for example at 1, 7, 14 and 30 days post-injection using the same evaluation procedure on each day. One or more measurements, for example about five, can be obtained for each subject at each time point. When measuring IOP according to methods known in the art, for example the method described above, IOP is shown to be reduced by, for example, at least about 10%, or at least about 30%, or at least about 50% over what is observed when a drug delivery system using an uncoated particle, for example a particle that is otherwise similar to the coated particle, is administered to the patient. To measure inflammation, Slit-lamp biomicroscopy can be performed to examine any eye compartment disclosed herein, for example, the AC, for signs of inflammation. The examination can involve observation of criteria such as the presence of cells, flare and fibrin. The subjects can be evaluated on several post-injection days, for example at 1, 7, 14 and 30 days post-injection using the same evaluation procedure on each day. After general and/or local anesthesia is achieved, each subject can be examined for gross abnormalities. The exams can be performed by the same trained ophthalmologist, and the ophthalmologist can be blinded to the assignment of the treatment and control subjects. Quantification of inflammation of an eye compartment such as the AC can be performed using a modified version of the Standard Uveitis Nomenclature clinical grading scheme, as detailed more fully in the examples. When measuring inflammation according to methods known in the art, for example the method described above, inflammation is shown to be reduced by, for example, at least about 10%, or at least about 30%, or at least about 50% over what is observed when a drug delivery system using an uncoated particle, for example a particle that is otherwise similar to the coated particle, is administered to the patient. When comparing an IOP or inflammation measurement obtained after administration of a coated particle versus an IOP or inflammation measurement obtained for an uncoated particle, the measurements compared can, and frequently should, be taken at similar time points post injection. For example, an IOP measurement for a coated particle taken 7 days post-injection is generally compared with an IOP measurement for an uncoated particle taken 7 days post-injection.

A further advantage of certain embodiments of the drug delivery systems disclosed herein is that they can be composed of generally recognized as safe (GRAS) materials, without the formation of new chemical entities (NCEs). Avoidance of NCE formation can be an advantage because NCEs can be subject to a lengthy and expensive regulatory review process before they are permitted to be marketed.

As described in detail in the Examples, the particle compositions can be retained within an eye compartment, including for example the stroma, the anterior chamber or the vitreous chamber for periods of time greater than those observed with free-standing drugs. Furthermore, coated particle compositions can exhibit increased retention over uncoated particle compositions. This effect is seen in particles with covalently-attached coatings, for example PEG-coated particles, as well as in particles with non-covalently associated coatings, of which Pluronic® PF-127-coated particles are representative, and indeed the extent of the effect can be very similar for covalently-attached and non-covalently associated coatings (see FIG. 1). FIG. 1 also demonstrates that this effect is also seen in particle compositions made with PLGA particles as well as those made with polystyrene particles. Furthermore, the increased retention is observed with polystyrene particles covalently coated with PEG coating as well as in PLGA particles with non-covalently associated Pluronic® PF-127 coating. Accordingly, where increased retention is demonstrated for one type of particle composition, for example, covalently-PEGylated polystyrene particles—one of ordinary skill in the art may expect that similar results would be obtained for other types of particle compositions, e.g., PLGA particles non-covalently coated with a poloxamer. For instance, as shown in the examples, PEGylated polystyrene particles behave similarly to and can serve as a model for PLGA particles with non-covalently associated coatings such as Pluronic® PF-127 coating. These findings are consistent with the art usage of polystyrene particles as models for other biocompatible particles and polymers.

Topically-administered medications to the eye often exhibit a poor ability to penetrate the corneal stroma. Further, free-standing drugs, when injected into the corneal stroma, are cleared rapidly by diffusion, thereby limiting the amount of time the medication remains at therapeutic concentrations at the site of the injection. In some embodiments, the presently disclosed subject matter demonstrates, for example, that intrastromally injected particle compositions can be retained with the corneal stroma for periods of time greater than free-standing drugs. For example, 200-nm and 1-μm latex particles injected intrastromally into living rabbits exhibited approximately 20% retention after two weeks. Uncoated 200-nm latex particles, however, caused substantial fibrin aggregation suggestive of inflammation after intraocular injection in living rabbits. By varying size and surface chemistry in accordance with the principles set forth herein, particles can be engineered to reduce or avoid corneal inflammation and edema.

In some embodiments, the presently disclosed subject matter includes delivery systems for intrastromal injection of medications that are combined with the particles disclosed herein. Medications can include, but are not limited to, anti-inflammatory agents, antimicrobial agents, anti-angiogenesis agents, immunosuppressants, and/or combinations thereof. Such combinations of medications can allow for the treatment of conditions that require more than one medication. More particularly, in some embodiments, the presently disclosed subject matter includes particle compositions containing anti-inflammatory agents for treating and/or preventing inflammatory processes of the cornea. Some embodiments of the presently disclosed subject matter include particle compositions containing immunosuppressant agents for preventing graft rejection after corneal transplantation.

In some embodiments, the presently disclosed subject matter includes particles coated with and/or otherwise carrying antibodies, wherein the antibodies serve as a therapeutic agent and can be released over time. In some embodiments, the presently disclosed subject matter includes particles combining a therapeutic antibody coating with other therapeutic agents, e.g., one or more medications.

Further, the presently disclosed subject matter includes pharmaceutical formulations including solutions of the presently disclosed particle compositions, wherein the particles are combined with antibacterial agents, antifungal agents, anti-amoebic agents, antiviral agents, and combinations thereof for treating and/or preventing infectious processes of the cornea. The presently disclosed subject matter also includes pharmaceutical formulations including solutions of the presently disclosed particle compositions containing and/or coated with anti-angiogenesis agents (such as, for example, antibodies) for use in chronic inflammatory diseases of the cornea and/or other diseases that can lead to corneal neovascularization. Combinations of the above-mentioned pharmaceutical formulations also are contemplated by the presently disclosed subject matter.

In a representative embodiment, the presently disclosed subject matter provides methods for treating keratitis, i.e., inflammations of the cornea, by injecting the presently disclosed particle compositions containing one or more therapeutic agents into the corneal stroma. Conditions treated by the presently disclosed methods include, but are not limited to, amoebic keratitis, fungal keratitis, bacterial keratitis, viral keratitis, and onchorcercal keratitis.

Amoebic keratitis can be caused by acanthamoeba and can be treated by administering to the corneal stroma of a subject in need of treatment thereof the presently disclosed particle compositions containing one or more anti-amoebic agents. Any anti-amoebic agent known in the art can be combined with the presently disclosed particle compositions. Representative, anti-amoebic agents include, but are not limited to, polyhexamethylene biguanide (PHMB), propamidine isethionate, miconazole nitrate, neomycin, chlorhexidine digluconate, polymicin B, clortrimazole, and combinations thereof.

Fungal keratitis can be caused by, for example, aspergillus fumigates, fusarium, and/or yeasts, such as candida, and can be treated by administering to the corneal stroma of a subject in need of treatment thereof the presently disclosed particle compositions containing one or more anti-fungal agents. Any anti-fungal agent known in the art can be combined with the presently disclosed particle compositions. Representative, anti-fungal agents include, but are not limited to, natamycin, nystatin, amphotericin B, chlorhexidine, fluorinated pyrimidines, such as flucytosine, azoles, such as imidazoles and triazoles, including, but not limited to, ketoconazole, miconazole, itraconazole, fluconazole, econazole, and clotrimazole, and combinations thereof.

Bacterial keratitis can be caused, for example, by *Streptococcus, Pseudomonas*, Enterobacteriaceae (including *Klebsiella, Enterobacter, Serratia*, and *Proteus*), and *Staphylococcus* species. Such infections can be treated by administering to the corneal stroma of a subject in need of treatment thereof the presently disclosed particle compositions containing one or more anti-bacterial agents. Any anti-bacterial agent known in the art can be combined with the presently disclosed particle compositions. Representative, anti-bacterial agents include, but are not limited to, cephalosporins, macrolides, glycopeptides, sulfonamides, chloramphenicol, fluoroquinolines, including, but not limited to, levofloxacin, gatifloxacin, moxifloxacin, and ofloxacin, and combinations thereof.

Further, up to 20% of cases of fungal keratitis (particularly candidiasis) can be complicated by bacterial co-infection. Thus, in some embodiments, the presently disclosed methods include combination therapies involving administering to the corneal stroma of a subject in need of treatment thereof the presently disclosed particle compositions containing one or more anti-fungal agents and one or more anti-bacterial agents.

Viral keratitis can, for example, be caused by a herpes simplex virus and can be treated by administering to the corneal stroma of a subject in need of treatment thereof the presently disclosed particle compositions containing one or more anti-viral agents. Any anti-viral agent known in the art can be combined with the presently disclosed particle compositions. A representative anti-viral agent includes, but is not limited to, acyclovir.

Onchoceral keratitis, also referred to as "River Blindness," is caused by the nematode *Onchocerca volvulus* and can be treated by administering to the corneal stroma of a subject in need of treatment thereof the presently disclosed particle compositions containing one or more anti-parasitic agents. Any anti-parasitic agent known in the art can be combined with the presently disclosed particle compositions. A representative anti-parasitic agent includes, but is not limited to, ivermectin.

Further, representative embodiments of the presently disclosed methods include a method for reversing or preventing graft rejection following corneal transplantation, the method involving administering to the corneal stroma of a subject in need of treatment thereof the presently disclosed particle compositions containing one or more immunosuppressive agents. Any immunosuppressive agent known in the art can be combined with the presently disclosed particle compositions. Representative immunosuppressive agents include, but are not limited to, corticosteroids, such as dexamethasone and prednisolone acetate.

In some embodiments, the presently disclosed subject matter demonstrates that, rather than injecting free-standing drugs into the anterior chamber (AC) of an eye, particles injected into the AC can be retained for at least several weeks. The time period spans the entire duration of typical post-operative treatment. By delivering medications combined with the presently disclosed particle compositions, the limitations of topical and intracameral free drug injection can be eliminated. This approach was limited in the past by particle-mediated increase in intraocular pressure (IOP) and inflammation responses. The presently disclosed subject matter overcomes these limitations by suitably modifying particle size and/or surface chemistry.

For example, the presently disclosed subject matter demonstrates that particles injected directly into the AC of an eye can be retained for long periods of time, thereby providing an effective vehicle for sustained ocular drug delivery. For example, the presently disclosed subject matter demonstrates that 200-nm latex particles, covalently coated with a representative coating such as, for example, poly(ethylene glycol), can be retained in the eyes of living rabbits for at least four weeks with greater than 30% retention. Based on experiments disclosed herein, other coated particles described herein, for example PLGA non-covalently coated with poloxamer, can bring about similar outcomes. In contrast, free drugs injected into the AC are cleared rapidly, for example, at the same rate as the aqueous humor turnover.

Further, uncoated 200-nm latex particles caused substantial fibrin aggregation in the AC of living rabbits. The presently disclosed subject matter demonstrates that by suitably modifying size and/or surface chemistry, particles can be engineered to avoid causing an increase in IOP and inflammation in the AC. For example, the presently disclosed subject matter demonstrates that 200-nm latex particles, covalently coated with PEG, did not induce an increase in IOP after injection into the AC of a living rabbit. Based on experiments disclosed herein, other coated particles described herein, for example PLGA non-covalently coated with poloxamer, can bring about similar outcomes.

In some embodiments, the presently disclosed subject matter includes medications for intracameral injection combined within particles including, but not limited to, anti-inflammatory drugs, antimicrobials, anti-angiogenesis agents, immunosuppressants, and/or combinations thereof. Such combinations of medications can allow for the treatment of conditions that require more than one medication. For example, the presently disclosed subject matter includes particle compositions containing anti-inflammatory agents alone or included with anti-angiogenesis agents for treating chronic corneal and/or anterior chamber inflammatory processes. In some embodiments, the presently disclosed subject matter provides particle compositions containing immunosuppressant agents either alone or in combination with anti-inflammatory agents and/or antimicrobial agents for use in post-corneal transplant cases.

Further, the presently disclosed subject matter includes pharmaceutical formulations containing solutions of the presently disclosed particle compositions, wherein the particle compositions contain anti-inflammatory and/or antimicrobial agents for injection after cataract extraction or other ophthalmic surgeries. The presently disclosed subject matter also includes pharmaceutical formulations of solutions of the presently disclosed particle compositions, wherein the particle compositions contain antibacterial, antifungal, amoebicidal, antiviral agents, or combinations thereof, for treating chronic infectious processes of the cornea and/or the anterior chamber. Combinations of the above-mentioned pharmaceutical formulations also are contemplated by the presently disclosed subject matter.

For example, the presently disclosed subject matter provides a method for intracameral administration of the presently disclosed particle compositions containing one or more therapeutic agents to an anterior chamber of an eye of a subject in need of treatment thereof. Depending on the condition of the subject, the therapeutic agent can be selected from the group consisting of an antibiotic, e.g., vancomycin, amikacin, eftazidime, cefuroxime, moxifloxacin, or a steroid, e.g., triamcinolone, dexamethasone, and prednisolone. The presently disclosed particle compositions can be administered prophylactically to prevent or reduce the occurrence of a post-operative infection of the anterior chamber or can be administered therapeutically to treat an infection of the anterior chamber, e.g., endophthalmitis.

In some embodiments, the presently disclosed particle compositions can provide an effective vehicle for sustained drug delivery directly to the retina. For example, the presently disclosed subject matter demonstrates that 200-nm latex particles, coated with a representative coating such as, for example poly(ethylene glycol) covalently bound to the particles, can be retained in the eyes of living rabbits for more than one month with no significant clearance and for over two months with only minimal clearance.

Further, the presently disclosed subject matter shows that uncoated 200-nm latex particles caused substantial fibrin aggregation suggestive of inflammation after intraocular injection in living rabbits. Also, uncoated 200-nm latex particles were found to cause visible vitreous opacities after intravitreal injection in living rabbits. By suitably modifying size and/or surface chemistry, the presently disclosed particle compositions can be engineered to avoid visual obstruction and inflammation in the vitreous chamber.

Other sustained release drug systems, when injected subconjunctivally, afford limited intraocular bioavailability of delivered medications due to barriers to drug penetration. Further, free drugs, when injected into the vitreous require multiple injections per year due to drug metabolism and clearance. In contrast, the presently disclosed particle compositions, when injected into the vitreous, can be retained for long periods of time.

In some embodiments, the presently disclosed subject matter includes medications combined with particles, wherein the medications include, but are not limited to, anti-inflammatory drugs, antimicrobials, anti-angiogenesis agents, immunosuppressants, anti-neoplastic agents and/or combinations thereof. Such combinations allow for the treatment of conditions that require more than one medication.

More particularly, the presently disclosed subject matter includes particle compositions containing anti-inflammatory agents for the treatment and/or prevention of macular edema and/or other inflammatory diseases of the retina. In some embodiments, the presently disclosed subject matter includes particle compositions containing anti-neoplastic agents for treatment of intraocular cancers. In yet other embodiments, the presently disclosed subject matter includes particle compositions containing immunosuppressant agents for the treatment of autoimmune and/or inflammatory diseases of the retina.

In other embodiments, the presently disclosed subject matter includes particles coated with and/or otherwise carrying antibodies, wherein the antibodies are a therapeutic agent and can be released over time. In yet other embodiments, the presently disclosed subject matter includes particles combining a therapeutic antibody coating with other therapeutic agents, e.g., one or more medications.

The presently disclosed subject matter also includes pharmaceutical formulations for intravitreal injection containing solutions of the presently disclosed particle compositions containing and/or coated with anti-angiogenesis agents (antibodies) for use in degenerative diseases of the retina and/or proliferative retinopathy and/or other vascular diseases of the retina. Some representative embodiments include pharmaceutical formulations containing solutions of particle compositions containing anti-inflammatory and/or antimicrobial agents for the prevention and/or treatment of post-surgical complications and/or infections after vitreoretinal operations. Further, pharmaceutical formulations containing solutions containing antibacterial and/or antifungal and/or anti-amoebic and/or antiviral agents for treatment of infectious processes of the vitreous and/or retina, including, but not limited to, endophthalmitis also are disclosed. Combinations of the above-mentioned pharmaceutical formulations also are contemplated by the presently disclosed subject matter.

For example, the presently disclosed subject matter provides a method for treating age-related macular degeneration in a subject in need of treatment thereof, the method involving administering via intravitreal injection to a vitreous chamber and/or retina of an eye of the subject the presently disclosed particle compositions containing one or more therapeutic agents selected from the group consisting of anti-vascular endothelial growth factor (VEGF) agents, including, but not limited to pegaptanib, bevacizumab, anecortane acetate, squalamine lactate, ranibizumab, or corticosteroids, including, but not limited to, triamcinolone acetonide.

In other embodiments, the presently disclosed subject matter provides a method for treating proliferative diabetic retinopathy in a subject in need of treatment thereof, the method involving administering via intravitreal injection to a vitreous chamber and/or retina of an eye of the subject the presently disclosed particle compositions containing one or more therapeutic agents selected from the group consisting of steroids, such as triamcinolone acetonide, ovine hyaluronidase. VEGF antibodies, such as bevacizumab, or VEGF antibody fragments, such as ranibizumab, and combinations thereof.

In yet other embodiments, the presently disclosed subject matter provides a method for treating ocular cancer in a subject in need of treatment thereof, the method involving administering via intravitreal injection to a vitreous chamber and/or retina of an eye of a subject the presently disclosed particle compositions containing one or more anti-neoplastic agents. Representative anti-neoplastic agent include, but are not limited to, fluoropyrimidine, pyrimidine nucleoside, platinum analogue, anthracycline, anthracenedione, epipodophyllotoxin, camptothecin, vinca alkaloid, and combinations thereof.

The particles according to the compositions and methods disclosed herein can be of any size that is consistent with effective treatment of the eye disorders disclosed herein, in the judgment of a person of ordinary skill in the art. For example, particles of any size can be used provided they do not obstruct the flow of intraocular fluids into and/or out of the eye compartment into which the particle composition is administered, which could increase inflammation or IOP. Particles having a diameter of, for example, from about 1 nm to about 100,000 nm, or from about 1 nm to about 50,000 nm, or from about 50 nm to about 50,000 nm, or from about 1 nm to about 30,000 nm, or from about 1 nm to about 10,000 nm, or from about 1 nm to about 1,000 nm, can be used according to the compositions and methods disclosed herein. Particles having a diameter of, for example, at least about 1 nm, at least about 10 nm, at least about 50 nm, at least about 100 nm, at least about 300 nm, at least about 500 nm or more can be used. Particles having a diameter of less than about 100,000 nm, or less than about 50,000 nm, or less than about 25,000 nm, or less than about 10,000 nm, or less than about 6,000 nm, or less than about 5,000 nm, or less than about 2,000 nm, or less than about 1,000 nm, or less than about 800 nm, or less than about 600 nm, or less than about 500 nm, or less than about 200 nm can be used. Particles of different diameters may be appropriate for administration to different eye compartments. For example, particles for intravitreal administration can have a diameter of at least about 1 nm, or from about 1 nm to about 50,000 nm, or any other diameter range disclosed herein. Particles for administration into the anterior chamber can have a diameter of, for example, from about 1 nm to about 7,000 nm, or from about 10 nm to about 6,000 nm, or from about 100 nm to about 2,000 nm, or from about 600 to about 1000 nm; or less than about 6,000 nm, or less than about 2,000 nm, or less than about 1,000 nm, or less than about 800 nm.

In some embodiments, the drug delivery system can include, for example, (i) a substrate; and (ii) a coating associated with the substrate. As used herein, a "substrate" is any substance, device or apparatus that can be coated according to the compositions and methods disclosed herein and thereafter administered to a patient. A substrate can be, for example, a medical device or an implant, or a particle as described herein. The substrate can be of any size that is consistent with effective delivery of a therapeutic agent to a patient, in the judgment of a person of ordinary skill in light of the compositions and methods disclosed herein. A substrate can have a diameter of, for example, at least about 1 nm, or at least about 1 micron, or at least about 1 mm, or at least about 10 mm; or from about 1 nm to about 10 mm, or from about 1 nm to about 1 mm, or from about 1 nm to about 100 microns, or from about 1 nm to about 10 microns, or from about 1 nm to about 1 micron. A substrate can be, for example, suitable for administration to a patient by any means known in the art, for example by injection or other form of systemic administration, whether rectally, transmucosally, transnasally, intestinally, parenterally, intramuscularly, subcutaneously, intramedullarily, intrathecally, intraventricularly, intravenously, intraperitoneally, iniranasally, intraocularly, or transurethrally; or topically; or via implantation into any region of the body of a patient. In some embodiments, the coating presents a hydrophilic region to the environment around the substrate. The drug delivery system can include, for example, a therapeutically effective amount of a therapeutic agent. The drug delivery system can, for example, bring about reduced inflammation when administered to the patient than if a drug delivery system comprising an uncoated particle were administered to the patient. As would be appreciated by a person of ordinary skill, the compositions and methods disclosed herein can be applied to drug delivery systems of any size range, up to and including of a size suitable for implants, including for example, intraocular implants, or the like.

The drug delivery system can also include, for example, (i) a substrate; (ii) a coating associated with the substrate, wherein the coating presents a hydrophilic region to the environment around the substrate; and (iii) a therapeutically effective amount of a therapeutic agent. In some embodiments, the drug delivery system is suitable for administration to a patient. The drug delivery system can, for example, bring about reduced inflammation when administered to the patient than if a drug delivery system comprising an uncoated substrate were administered to the patient.

In some embodiments the particles of the compositions and methods disclosed herein are nanoparticles. As used herein, the term "nanoparticle" refers to a particle having at least one dimension in the range of about 1 nm to about 1000 nm, including any integer value between 1 nm and 1000 nm (including about 1, 2, 5, 10, 20, 50, 60, 70, 80, 90, 100, 150, 200, 250, 300, 400, 500, 600, 700, 800, 900 and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle." As used herein, "microparticle" refers to a particle having at least one dimension in the range of about 1 μm to about 100 μm, including any integer value between 1 μm and 100 μm (including about 1, 2, 5, 10, 20, 30 40, 50, 60, 70, 80, 90 and 100 μm and all integers and fractional integers in between). Exemplary microparticles have a diameter of less than about 100 microns, less than about 50 microns, less than about 10 microns, less than about 5 microns, or less than about 3 microns, or less than about 2 microns. The term "particle" as used herein is meant to include nanoparticles and microparticles.

It will be appreciated by one of ordinary skill in the art that particles suitable for use with the presently disclosed methods can exist in a variety of shapes, including, but not limited to, spheroids, rods, disks, pyramids, cubes, cylinders, nanohelixes, nanosprings, nanorings, rod-shaped particles, arrow-shaped particles, teardrop-shaped particles, tetrapod-shaped particles, prism-shaped particles, and a plurality of other geometric and non-geometric shapes. In some embodiments, the presently disclosed particles have a spherical shape.

In some embodiments, the presently disclosed particles include polystyrene particles. For example, the presently disclosed particles include carboxyl-modified polystyrene particles. The presently disclosed particles in some embodiments can be tagged, e.g., with a fluorescent molecule, to enable them to be detected or monitored when administered to a subject. For example, in some embodiments, the particles include yellow-green fluorescent carboxyl-modified polystyrene particles (Molecular Probes, Eugene, Oreg.).

Further, in some embodiments, the presently disclosed particles can be surface modified, e.g., by covalently attaching PEG, often referred to as being PEGylated. Such particles can be prepared as disclosed in Lai et al., "Rapid transport of large polymeric nanoparticles in fresh undiluted human mucus," *Proc. Natl. Acad. Sci. U.S.A.*, 104(5):1482-

1.487 (2007) and Suh et al., "PEGylation of nanoparticles improves their cytoplasmic transport," *Int. J Nanomed.*, 2(4), 735-741 (2007).

For example, one 100- to 500-nm yellow-green fluorescent, carboxyl-modified polystyrene (PS) particles (Molecular Probes, Eugene, Oreg.) can be dialyzed extensively against PBS (300 kDa, Spectrum Lab, Rancho Dominguez, Calif.). Polyethylene glycol can be covalently attached to the particles via carboxyl-amine reaction. Briefly, diamine PEG (molecular mass >2,000 Da, e.g., 3,400 Da; Nektar Therapeutics, San Carlos, Calif.) can be dissolved in 50 mM 2-(N-morpholino)ethanesulfonic acid (MES) buffer (Sigma, St. Louis, Mo.) at pH 6. PEG can be added to different sized nondialyzed particles to yield final concentrations of 3:1 PEG:COOH and 1% solids/mL. After 15 minutes, 1-ethyl-3-(3-dimethylaminopropyl)-carbodiimide (Sigma, St Louis, Mo.) can be added to a final concentration of 4 mg/mL, pH adjusted to 6.5, and incubated on an orbital shaker for 2 hours at room temperature. To quench the reaction, glycine (J. T. Baker, Phillipsburg, N.J.) can be added to a final concentration of 100 mM. The solution can be incubated for 30 minutes at room temperature and subsequently dialyzed extensively against PBS in a 300,000 kDa MWCO Float-a-lyzer (Spectrum Laboratories, Rancho Dominguez, Calif.). Unmodified particles were dialyzed similarly to remove all traces of sodium azide originally added by the manufacturer.

Size and $\xi$-potential can be determined by dynamic light scattering and laser Doppler anemometry, respectively, using, for example, a Zetasizer 3000 (Malvern Instruments, Southborough, Mass.). Size measurements can be performed, for example, at 25° C. at a scattering angle of 90°. Samples can be further diluted in double-distilled water.

Representative characteristics of particles prepared by the method of Lai et al. are summarized in Table 1.

TABLE 1

Representative Characteristics of COOH– and PEG-Modified PS Particles

| Nominal Size (nm) | Surface Chemistry | Diameter (nm) | $\xi$-potential (mV) |
| --- | --- | --- | --- |
| 100 | COOH | 109.2 ± 3.1 | −41.0 ± 1.9 |
| 100 | PEG | 122.4 ± 5.2 | −4.4 ± 1.1 |
| 200 | COOH | 216.6 ± 4.5 | −58.8 ± 4.2 |
| 200 | PEG | 232.3 ± 6.8 | −2.1 ± 0.3 |
| 500 | COOH | 515.0 ± 7.2 | −61.0 ± 0.5 |
| 500 | PEG | 529.1 ± 8.1 | −5.6 ± 0.4 |

In certain embodiments, the particles can be combined with an active ingredient, e.g., a drug, medication, or therapeutic agent. Active ingredients include, but are not limited to, any component, compound, or small molecule that can be used to bring about a desired effect, e.g., a therapeutic effect. For example, a desired effect can include the diagnosis, cure, mitigation, treatment, or prevention of a disease or condition.

The active ingredient can be adsorbed, encapsulated, entangled, embedded, incorporated, bound to the surface, or otherwise associated with the particle. As used herein, "combined" encompasses adsorbed, encapsulated, associated, entangled, embedded, incorporated, bound to the surface, or any other means for holding two substances or items together. As provided hereinabove, in some embodiments the presently disclosed particles can include a functional group, e.g., a carboxyl group. Other functional groups include, but are not limited to, a sulhydryl, hydroxyl, and/or amino group. The functional groups can be available, for example, for drug binding (covalent or electrostatic) or for other desired purposes within the scope of the presently disclosed subject matter.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The terms "treat" or "treating," and grammatical derivatives thereof, as used herein refer to any type of treatment that imparts a benefit to a subject afflicted with a disease or illness, including any measurable improvement in the condition of the subject, reducing a symptom of the condition, inhibiting an underlying cause or mechanism related to the condition, delaying the progression of the condition, preventing or delaying the onset of the disease or illness, e.g., prophylactic treatment, enhancing normal physiological functionality, and the like. Thus, treating does nor require a cure.

The term "effective," as that term is used in the specification and/or claims, means adequate to accomplish a desired, expected, or intended result. More particularly, a "therapeutically effective amount" as provided herein refers to an amount of the presently disclosed particle compositions necessary to provide the desired therapeutic effect, e.g., an amount that is effective to prevent, alleviate, ameliorate or otherwise treat symptoms of disease or prolong the survival of the subject being treated. As would be appreciated by one of ordinary skill in the art upon review of the present disclosure and as provided in more detail herein below, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The presently disclosed particle compositions can be administered therapeutically to achieve a therapeutic benefit or prophylactically to achieve a prophylactic benefit. By therapeutic benefit is meant treating the underlying disorder including eradication or amelioration of one or more of the symptoms associated with the underlying disorder such that the patient reports an improvement in feeling or condition, notwithstanding that the patient can still be afflicted with the underlying disorder. For example, administration of a particle composition to a patient suffering from a condition provides therapeutic benefit not only when the underlying condition is eradicated or ameliorated, but also when the patient reports a decrease in the severity or duration of the symptoms associated with the condition. Therapeutic benefit also includes halting or slowing the progression of the disease, regardless of whether improvement is realized by the patient.

For prophylactic administration, the presently disclosed particle compositions can be administered to a subject at risk of developing a particular ocular condition or disorder. Alternatively, prophylactic administration can be applied to avoid the onset of symptoms in a patient diagnosed with the underlying condition or disorder.

The amount of the presently disclosed particle compositions administered to a subject will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular therapeutic agent as measured in an in vitro assay known in the art. Calculating dosages to achieve such circulating blood or serum concentrations taking into account the bioavailability of the particular compound is well within the capabilities of skilled artisans. For guidance, see Fingl & Woodbury, "General Principles," In: Goodman and Oilman's The Pharmaceutical Basis of Therapeutics, Chapter 1, pp. 1-46, latest edition, Pagamonon Press, and the references cited therein.

Initial dosages also can be estimated from in vivo data, such as animal models. Animal models useful for testing the efficacy of therapeutic agents to treat or prevent the various diseases described above are well-known in the art. Dosage amounts will depend on, among other factors, the activity of the therapeutic agent, its bioavailability, the mode of administration and various factors discussed above. Dosage amount and interval can be adjusted individually to provide levels of the therapeutic agents(s) sufficient to maintain a therapeutic or prophylactic effect. Skilled artisans will be able to optimize effective local dosages without undue experimentation.

The presently disclosed particle compositions can be administered once per day, a few or several times per day, or even multiple times per day, depending upon, among other things, the indication being treated and the judgment of the prescribing physician.

Preferably, the presently disclosed particle compositions will provide therapeutic or prophylactic benefit without causing substantial toxicity. Toxicity of the particle compositions can be determined using standard pharmaceutical procedures. The dose ratio between toxic and therapeutic (or prophylactic) effect is the therapeutic index. Compositions that exhibit high therapeutic indices are preferred.

As provided hereinabove, the presently disclosed particles, in particular embodiments, will contain one or more "active compounds" or "therapeutic agents." Pharmaceutical compositions containing the presently disclosed particle compositions also are provided herein.

These pharmaceutical compositions include the presently disclosed active compounds in a pharmaceutically acceptable carrier. The term "pharmaceutically acceptable" with respect to a component, such as a salt, carrier, excipient or diluent of a composition according to the presently disclosed subject matter refers to a component that is compatible with the other ingredients of the composition in that it can be combined with the presently disclosed particle compositions without eliminating the therapeutic efficacy of the active compounds or therapeutic agents and is suitable for use with subjects as provided herein without undue adverse side effects (including, but not limited to, toxicity, irritation, and allergic response) to the subject to which the particular particle composition is administered. Examples of pharmaceutically acceptable components include, without limitation, any of the standard pharmaceutical carriers, such as phosphate buffered saline solutions, water, emulsions such as oil/water emulsion, microemulsions, and various types of wetting agents.

When used to treat or prevent conditions and diseases as described herein, the presently disclosed active compounds can be administered singly, as mixtures of one or more active compounds or in mixture or combination with other agents useful for treating such diseases and/or the symptoms associated with such diseases.

Further, in representative embodiments, certain active compounds and/or therapeutic agents disclosed herein are prodrugs. The term "prodrug" refers to a therapeutic agent that has been chemically derivatized such that, upon administration to a subject, the derivative is metabolized to yield the biologically-active therapeutic agent. Accordingly, upon administration to a recipient, a prodrug is capable of providing (directly or indirectly) a compound of the presently disclosed subject matter or an inhibitorily active metabolite or residue thereof. Prodrugs can increase the bioavailability of the presently disclosed compounds when such compounds are administered to a subject (e.g., by allowing an orally administered compound to be more readily absorbed into the blood) or can enhance delivery of the parent compound to a biological compartment (e.g., the brain or lymphatic system) relative to a metabolite species.

Pharmaceutical compositions containing the presently disclosed particle compositions, including active compounds (or prodrugs thereof), can be manufactured by means of conventional mixing, dissolving, granulating, dragee-making levigating, emulsifying, encapsulating, entrapping and/or lyophilization processes. The presently disclosed pharmaceutical compositions can be formulated in conventional manner using one or more physiologically acceptable carriers, diluents, excipients or auxiliaries that facilitate processing of the active compounds into preparations that can be used pharmaceutically.

Useful injectable compositions containing the presently disclosed particle compositions include sterile suspensions, solutions or emulsions of the active compound(s) in aqueous or oily vehicles. The compositions also can contain formulating agents, such as suspending, stabilizing and/or dispersing agents. The compositions suitable for injection can be presented in unit dosage form, e.g., in ampules or in multidose containers, and can contain added preservatives. Alternatively, an injectable composition can be provided in powder form for reconstitution with a suitable vehicle, including, but not limited to, sterile water, buffer, dextrose solution, and the like, before use. To this end, the presently disclose particles can be dried by any art-known technique, such as lyophilization, and reconstituted prior to use.

In addition to the presently disclosed particle compositions, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain anti-microbial preservatives. Useful anti-microbial preservatives include methylparaben, propylparaben, and benzyl alcohol. The anti-microbial preservative is typically employed when the formulation is placed in a vial designed for multidose use.

EXAMPLES

The presently disclosed subject matter now will be described more fully hereinafter with reference to the accompanying Examples, in which some, but not all embodiments of the inventions are shown. The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Preparation and Characterization of PEG-Coated Particles

Fluorescent, carboxyl-modified polystyrene particles (Molecular Probes, Eugene, Oreg.) were covalently modified with 2-3.4 kDa amine-modified PEG (Nektar Therapeutics, San Carlos, Calif.) via a carboxyl-amine reaction, as previously published. Unconjugated PEG was removed by three rounds of washing and centrifugation. The PEG-coated particles were stored at 4° C. until use. A near-neutral 4-potential measured by Doppler anemometry was used to confirm PEG conjugation. These particles are also referred to herein as coated latex particles.

Example 2

Particle Administration to the Corneal Stroma

Particles according to Example 1 were administered to the corneal stroma in one of two ways depending on the most appropriate dose for a clinical situation. Direct intrastromal injections were used to provide smaller volumes of particle solution to the cornea. Such injections involved insertion of a small gauge needle into the stromal layer of the cornea. These injection sites are most often self sealing. They can, however, be closed with the aid of corneal glue and/or contact lens placement if leakage occurs.

Larger doses of particles were administered by first creating a pocket in the corneal stroma. The pocket was created outside the visual axis and the size was determined based on the required dose. The particles were then administered directly into the pocket, which was then closed with corneal glue and placement of a contact lens for the first postoperative day.

Example 3

Particle Administration to the Anterior Chamber

Intraoperative Injection

Small incisions are created in the cornea during cataract extraction surgery. These incisions, which are used for removing the cataractous lens and implanting the artificial lens, are closed by a process of hydrosealing at the end of surgery. The particles are injected into the AC through the surgical incision and sealed in the chamber once the wound is closed.

Non-Operative Administration

A small gauge needle was inserted through the peripheral cornea and used to inject the solution of particles according to Example 1 into the AC. These injection sites are most commonly self-sealing, however, corneal glue and/or contact lens placement were used for the first 24 hours to prevent leakage.

Example 4

Particle Administration into the Vitreous Chamber

Injections of particle solutions into the vitreous chamber were performed through the pars plana, an anatomic location that is devoid of vasculature and retinal tissue, limiting the risk of bleeding and retinal and/or lens injury. A small gauge needle was used to inject particles according to Example 1. Injection sites of this size are self sealing, eliminating the need for closure. Injections were performed after first disinfecting and topically anesthetizing the site.

Example 5

Sustained and Targeted Drug Delivery with Intrasomal Microparticles and Nanoparticles for Treating Chronic Keratitis and Corneal Graft Rejection Purpose Many cases of amoebic and fungal keratitis, as well as corneal graft rejection, remain refractory to topical therapy. Intrastromal (IS) injection of medications has been introduced as an alternative to topical administration, but IS injection remains limited due to drug loss by diffusion and clearance. The presently disclosed subject matter demonstrates that IS administration of micro- and nanoparticles such as latex particles can be used for sustained delivery of antimicrobials or immunosuppressant agents to the cornea.

Methods

This embodiment included studying three groups, each with three rabbits. The three groups included: (a) a control group receiving 10 µL of saline into an intrastromal pocket; (b) a microparticle group receiving 10 µL of 1-µm particles covalently coated with PEG in the pocket; and (c) a nanoparticle group receiving 10 µL of 200-nm particles covalently coated with PEG into the pocket.

The retention of the particles was assessed by in vivo fluorescence. The images were obtained at zero (0) minutes; one hour; six hours; daily for one week; and every other day for fourteen days. The initial fluorescence value for each eye was used to determine the relative clearance of particles from the corneal stroma.

Results

Micro- and nanoparticles were cleared from the stroma at similar rates ($P<0.05$). At one hour, a clearance of 21% of the 1-µm particles and 23% of the 200-nm particles was observed. At 24 hours, a loss of 52% and 41% of the total injection 1-µm particles and 200-nm particles, respectively, was observed. The rate of clearance became more gradual with time: at 14 days, 79% and 73% of the original dose of the 1-µm particles and 200-nm particles were lost, respectively. The control group had no detectable fluorescence at any time point.

Conclusion

The observation that more than 20% of the presently disclosed particles are still present in the corneal stroma after 14 days indicates that IS micro- and nanoparticles provide a method for long-term delivery of medications to the cornea and could be useful in the management and treatment of chronic keratitis and graft rejection.

Example 6

Intracameral Injection of Particles for Sustained Delivery of Post-Operative Medications to the Anterior Chamber Purpose Intracameral (IC) administration of antimicrobial and anti-inflammatory agents during intraocular surgery has been proposed to decrease the need for post-operative topical drop. Free drugs, however, are cleared with the aqueous humor (AH). The presently disclosed subject matter demonstrates the use of particles for longer-term delivery of medications to the anterior chamber (AC), by evaluating the clearance rates and complications associated with the administration of IC particles.

Methods

Nine rabbit eyes were examined in this embodiment. Baseline fluorescence and intraocular pressures (IOP) were assessed. Groups included: (a) control—100 µL of IC saline; (b) uncoated—100 µL of IC 200-nm uncoated latex particles; and (c) coated—100 µL of IC 200-nm latex particle, which were coated with PEG. The particles were linked to fluorescence tags, which allowed detection by in vivo fluorescence. Fluorescence images and IOP measurements were obtained at zero (0) minutes; one hour; six hours; daily for one week; and every two days for one month. Relative particle retention was evaluated by comparing fluorescence images to those obtained a t=0.

Results

No fluorescence was detected in the control group. Particle loss was observed immediately after injection in both experimental groups: Significant percentages of both the coated and uncoated particles remained after one day and 15 days. After 30 days, 33% and 18% of the total particles were retained in the coated and uncoated groups, respectively. A significantly greater clearance of uncoated particles (P<0.05) was observed. Only one animal, from the uncoated group, developed elevated IOP after the injection, which resolved progressively within 16 days.

Conclusion

The presently disclosed subject matter demonstrates that intraoperative IC injection of particles of nano-size or larger can be a useful tool for providing sustained delivery of post-operative medications to the AC for as long as one month.

Example 7

Intravitreal Particles for the Sustained Treatment of Degenerative and Proliferative Diseases of the Retina Purpose Intravitreal injection of angiogenesis inhibitors has become commonplace in the treatment of retinal diseases, such as age-related macular degeneration and proliferative diabetic retinopathy. Unfortunately, this route of delivery requires repeated injections, increasing the risk of infection and retinal injury. The presently disclosed subject matter determines the length of time particles can be retained in the vitreous chamber after pars plana injection and demonstrates the use of the presently disclosed drug carriers for the long-term treatment of diseases of a retina.

Methods

The study was conducted on nine rabbit eyes and included three groups: (a) a control group received a 100-µL intravitreal injection of saline; (b) an uncoated group received 100 µL of intravitreal 200-nm uncoated latex particle solution; and (c) a coated group received 100 µL of intravitreal 200-nm latex particles coated with PEG. The baseline fluorescence and intraocular pressure (IOP) were assessed prior to injection through the pars plana. The particles were fluorescence tagged and assessment of retention was made by analysis of in vivo fluorescence imaging. Images and IOP measurements were obtained at zero (0) minutes, one hour, daily for one week, and every five days for one month. The fluorescence images from each time point were compared to those obtained immediately after the intravitreal injection to determine the relative retention rates for each eye.

Results

No significant differences between the clearance profiles of the coated and uncoated particles were observed. No significant decline in the particles retained in the vitreous chambers was observed over 30 days (P<0.05). No detectable fluorescence signal was observed in the control group. No changes in IOP were observed in any group.

Conclusion

The presently disclosed particles provide sustained and predictable release of medications and can be an effective system for long-term intravitreal drug delivery and the treatment of various retinal diseases.

Example 8

Inflammation Profile Following Intracameral Injection of Particles

Materials and Methods

Particle Synthesis

Fluorescent carboxyl-modified polystyrene particles 100-1000 nm in size (Molecular Probes, Eugene, Oreg.) were covalently conjugated with 2 kDa diamine PEG, according to methods known in the art.

PLGA (15 kDa) was fluorescently labeled with Alexa Fluor 647 cadaverine (AF647; Invitrogen Corporation, Carlsbad, Calif.) using a modified method, as previously described. Fluorescently labeled nanoparticles were formed by emulsion method. To form the emulsion, 100 mg of PLGA-AF647 dissolved in one ml of dichloromethane (DCM) was homogenized at 10 k rpm for 2 min in 15 ml of aqueous phase (2% PVA, 10% F127, or 10% F68), then added to 100 ml aqueous phase (0.1% PVA, 1% F127, or 1% F68) and stirred for 2 h to remove solvent. Particles were collected, washed twice, and resuspended.

Size and zeta-potential were determined by dynamic light scattering and laser Doppler anemometry, respectively, using a Zetasizer Nano ZS90 (Malvern Instruments).

Groups and Numbers

This study included 30 eyes from 30 New Zealand white rabbits. There were 5 experimental groups and one control group, each with n=5 animals. Two experimental groups received intracameral (IC) injections of polystyrene (PS)

particles; uncoated (PS-COOH) and coated with poly(ethylene) glycol (PS-PEG). Three groups received IC injections of biodegradable poly(lactic-co-glycolic acid, PLGA); one group had no pluronics coating (PLGA-PVA), another with moderate pluronics coating (PLGA-F68) and another with dense pluronics coating (PLGA-F127). The control group received a sham IC injection with phosphate buttered saline (PBS).

Pre-Injection Assessment

The intraocular pressure (IOP) and anterior chamber (AC) inflammation were evaluated in all animals to establish baseline levels before particle suspension injection. Animals with elevated IOP or any signs of inflammation were excluded from the study. The animals were anesthetized with an intramuscular injection (IM) of ketamine/xylazine solution. Once general anesthesia was achieved a drop of 0.5% proparacaine topical anesthetic solution was instilled onto the surface of the right eye of the animal and a wire eyelid speculum was placed to keep the lid open.

A Reichert Tono-Pen contact tonometer was used to assess the IOP; five measurements were obtained for each animal at each time point. A slit-lamp biomicroscope exam was then performed to examine the AC for signs of inflammation; criteria included presence of cells, flare and fibrin.

Injection Preparation

Injections were performed immediately after the particles were synthesized. The suspension was homogenized using a table-top lab vortex and doses of 120 μL were measured and pipetted into individual microcentrifuge tubes. The particle suspensions were vortexed again immediately prior to drawing them into the administration syringes. In order to ensure that none of the particle suspension was lost in the deadspace of the syringe/needle during injection, an air cushion was created between the plunger and the particle suspension by first drawing air into the syringe prior to the suspension.

Particle Injection

The animals were anesthetized as outlined above. Once general anesthesia was achieved, a drop of 0.5% proparacaine was instilled onto the right eye of the animal prior to placement of a wire eye lid speculum. A 30 gauge needle attached to an empty 1 cc Luer-lock syringe was inserted into the AC through the peripheral cornea using a narrow angle of approach, and 120 μL of aqueous humor (AH) was extracted. While holding the needle in the place in the AC, the extraction syringe was detached and the syringe containing the particle suspension (or control PBS) was attached to the needle and the contents were injected into the AC. The needle and syringe were quickly withdrawn and a drop of cyanoacrylate corneal glue was immediately placed on the injection site. The animals were monitored until anesthesia reversal, at which time they were returned to their cages.

Post-Injection Assessment

The animals were evaluated on post-injection days 1, 7, 14 and 30 and the same evaluation procedure was performed on each day. After general and local anesthesia were achieved, each animal was examined for gross abnormalities. IOP was measured as indicated above. Slit-lamp biomicroscopy was performed to evaluate and quantify AC inflammation. The exams were performed by the same trained ophthalmologist who was blinded to the assignment of the treatment and control animals. The AC inflammation was quantified using a modified version of the Standard Uveitis Nomenclature clinical grading scheme, as detailed below.

Modified Standardization of Uveitis Nomenclature (SUN) Scheme

| Part 1. Grading Scheme for Anterior Chamber Cells | |
|---|---|
| Grade | Cells in Field |
| 0 | <1 |
| 0.5 | 1-5 |
| 1 | 6-15 |
| 2 | 16-25 |
| 3 | 26-50 |
| 4 | >50 |

| Part 2. Grading Scheme for Anterior Chamber Flare | |
|---|---|
| Grade | Description |
| 0 | None |
| 1 | Faint |
| 2 | Moderate (iris and lens details clear) |
| 3 | Marked (iris and lens details hazy) |
| 4 | Intense (fibrin or plastic aqueous) |

| Part 3. Grading Scheme for Anterior Chamber Fibrin Reaction | |
|---|---|
| Grade | Fibrin Morphology |
| 0 | None |
| 1 | Spots, non-continuous |
| 2 | Lines or semi-transparent membranes |
| 3 | Flat opaque patches |
| 4 | Isometric masses |

Results

The mean inflammation scores for each group are presented below in Table 1 as well as in FIG. 1. At day 1 there was clinically visible AC inflammation in all animals in all groups, including the control group. The inflammation trend was similar for all groups: a rapid rise from the time of injection with a peak score at Day 1, followed by a progressive decline until the end of the study (Day 30).

The inflammation was significantly higher in the PS-COOH, PLGA-PVA, and PLGA-F68 groups compared to the PS-PEG, PLGA-F127 and Saline groups at all time points. There was no significant difference among the scores of PS-COOH, PLGA-PVA and PLGA-F68 groups (at any time point), and likewise there was no significant difference among the scores of the PS-PEG, PLGA-F127 and Saline (Control) groups at any time point ($P<0.05$).

TABLE 1

The mean AC inflammation scores from among the animals (n = 5) in each group for each time point evaluated in this study.

| Particle | Post Injection Day | | | | |
|---|---|---|---|---|---|
| | Day 0 | Day 1 | Day 7 | Day 14 | Day 30 |
| PS-COOH | 0 | 6.8 | 4.2 | 3.8 | 3.2 |
| PS-PEG | 0 | 5.4 | 2.8 | 1.8 | 1.2 |
| PLGA-PVA | 0 | 8.6 | 5 | 4.2 | 3.6 |
| PLGA-F68 | 0 | 7.8 | 4.4 | 3.8 | 3.4 |
| PLGA-F127 | 0 | 5.6 | 2.8 | 2 | 1.4 |
| Control | 0 | 5.2 | 2.2 | 1.8 | 1.1 |

Although the foregoing subject matter has been described in some detail by way of illustration and example for purposes of clarity of understanding, it will be understood by those skilled in the art that certain changes and modifications can be made without departing from the spirit and scope of the invention.

All publications, patent applications, patents, and other references are herein incorporated by reference to the same extent as if each publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

REFERENCES

Bourges et al., "Ocular drug delivery targeting the retina and retinal pigment epithelium using polylactide nanoparticles," *Investigative Ophthalmology & Visual Science (VIOS)*, 44(8):3562-3569 (2003);

De Kozak et al., "Intraocular injection of tamoxifen-loaded nanoparticles: a new treatment of experimental autoimmune uveoretinitis," *Eur. J. Immunol.*, 34:3702-3712 (2004);

Lai et al., "Rapid transport of large polymeric nanoparticles in fresh undiluted human mucus," *Proc. Natl. Acad Sci. USA.*, 104(5):1482-1487 (2007).

Sub et al., "PEGylation of nanoparticles improves their cytoplasmic transport," *Int. J. Nanomed.*, 2(4):735-741 (2007);

Yang et al., "Biodegradable nanoparticles composed entirely of safe materials that rapidly penetrate human mucus," *Agnew. Chem. Int. Ed*, 50:1-5 (2011);

U.S. Pat. No. 7,550,154 B2 to Saltzman et al. for "Methods of Treatment With Drug Loaded Polymeric Materials," issued Jun. 23, 2009;

U.S. Pat. No. 7,638,137 B2 to Chauhan et al. for "Ophthalmic Drug Delivery System," issued Dec. 29, 2009.

U.S. Pat. No. 7,645,736 B2 to Bender et al. for "Integrin inhibitors for the Treatment of Eye Diseases," issued Jan. 12, 2010;

U.S. Pat. No. 7,648,959 B132 to Bender et al. for "Methods and Compositions for the Treatment of Diseases of the Eye, issued Jan. 19, 2010;

U.S. Patent Application Publication No. US2007/0087989 A1 to Huang et al. for "Methods of Treating Ocular Conditions," published Apr. 19, 2007;

U.S. Patent Application Publication No. US2007/0238654 A1 to Deschatelets et al. for "Compstatin and Analogs thereof for Eye Disorders," published Oct. 11, 2007;

U.S. Patent Application Publication No. US2008/0287341 A1 to Chen for "Treatment of Vascular Abnormalities using Nanoparticles," published Nov. 20, 2008;

U.S. Patent Application Publication No. US2009/0011040 A1 to Naash et al. for "Use of Compacted Nucleic Acid Nanoparticles in Non-Viral Treatments of Ocular Diseases," published Jan. 8, 2009;

U.S. Patent Application Publication No. US2009/0220572 A1 to Deschatelets et al. for "Injectable Combination Therapy for Eye Disorders." Sep. 3, 2009;

U.S. Patent Application Publication No. US2009/0226531 A1 to Lyons et al. for "Methods and Composition for Intraocular Delivery of Therapeutic SiRNA," Sep. 10, 2009;

U.S. Patent Application Publication No, US2009/0291919 A1 to Kaushal et al. for "Compositions and Methods for Treating or Preventing Ophthalmic Light Toxicity," published Nov. 26, 2009; and U.S. Patent Application Publication No. US2010/0034749 A1 to Schulze et al, for "Use of Cationic Colloidal Preparation for the Diagnosis and Treatment of Ocular Diseases," published Feb. 11, 2010.

The invention claimed is:

1. A method for treating an eye disorder in a patient in need thereof, comprising administering by intravitreal injection into the vitreous chamber of the eye an effective amount of a drug delivery system which comprises:
   (i) microparticles including a core which includes the biodegradable polymer polylactide-co-glycolide;
   (ii) a coating non-covalently associated with the microparticles, wherein the coating comprises molecules having a hydrophilic region and a hydrophobic region, wherein the hydrophilic region is polyethylene glycol; and
   (iii) a therapeutically effective amount of an anti-angiogenic agent,
   wherein the drug delivery system provides sustained release of the anti-angiogenic agent into the vitreous chamber over a period of time of at least three months; and
   wherein the vitreous chamber of the eye exhibits at least 10% less inflammation or intraocular pressure than if the particles were uncoated, for at least about 30 days post-administration.

2. The method of claim 1, wherein the diameter of the microparticles is about 50 microns or less.

3. The method of claim 1, wherein the diameter of the microparticles is about 30 microns or less.

4. The method of claim 1, wherein the coating molecule is a block-copolymer.

5. The method of claim 1, wherein the microparticles consist essentially of polylactide-co-glycolide.

6. The method of claim 1, wherein the disorder is macular degeneration.

7. The method of claim 1, wherein the disorder is age-related macular degeneration.

8. The method of claim 1, wherein the disorder is diabetic retinopathy.

9. The method of claim 1, wherein the disorder is corneal neovascularization.

10. The method of claim 1, wherein the anti-angiogenic agent is released from the drug delivery system into the vitreous chamber of the patient's eye over a period of time of at least six months.

11. The method of claim 1, wherein the anti-angiogenic agent is an anti-vascular endothelial growth factor agent.

12. The method of claim 1, wherein the patient is a human.

13. The method of claim 1, wherein the drug delivery system is lyophilized and then reconstituted prior to administration by intravitreal injection.

14. The method of claim 1, wherein the drug delivery system is provided in a sterile suspension.

15. The method of claim 14, wherein the sterile suspension includes a suspending agent.

16. An injectable composition for administration to the vitreous chamber of the eye of a patient, comprising a drug delivery system that comprises:
   (i) microparticles having a diameter of 30 μm or less including a core which includes the biodegradable polymer polylactide-co-glycolide;
   (ii) a coating non-covalently associated with the microparticles, wherein the coating is formed of molecules having a polyethylene glycol hydrophilic region and a hydrophobic region;

(iii) a therapeutically effective amount of an anti-angiogenic agent;
(iv) in a sterile suspension suitable for intravitreal delivery;
wherein the drug delivery system provides sustained release of the anti-angiogenic agent into the vitreous chamber of the eye of the patient over a period of time of at least three months and
wherein the vitreous chamber of the eye exhibits at least 10% less inflammation or intraocular pressure than if the particles were uncoated, for at least about 30 days post-administration.

17. The injectable composition of claim 16, wherein the composition includes a suspending agent.

18. The injectable composition of claim 16, wherein the anti-angiogenic agent is an anti-vascular endothelial growth factor agent.

19. The injectable composition of claim 16, wherein the drug delivery system provides sustained release of the anti-angiogenic agent into the vitreous chamber of the eye over a period of time of at least six months.

20. The injectable composition of claim 16, wherein the patient is a human.

21. A drug delivery system for intravitreal injection into the vitreous chamber of the eye of a patient, comprising:
(i) microparticles having a diameter of 30 μm or less including a core which includes the biodegradable polymer polylactide-co-glycolide;
(ii) a coating non-covalently associated with the microparticles, wherein the coating comprises molecules having a hydrophilic region and a hydrophobic region, wherein the hydrophilic region is polyethylene glycol;
(iii) a therapeutically effective amount of a anti-angiogenic agent;
(iv) in a sterile suspension; and
(v) a device containing a needle for intravitreal injection;
wherein the drug delivery system provides sustained release of the anti-angiogenic agent into the vitreous chamber of the eye patient's over a period of time of at least three months and wherein the vitreous chamber of the eye exhibits at least 10% less inflammation or intraocular pressure than if the particles were uncoated for at least about 30 days post-administration.

22. The drug delivery system of claim 21, wherein the composition includes a suspending agent.

23. The drug delivery system of claim 21, wherein the anti-angiogenic agent is an anti-VEGF agent.

24. The drug delivery system of claim 21, wherein the drug delivery system provides sustained release of the anti-angiogenic agent into the vitreous chamber of the eye over a period of time of at least six months.

25. The drug delivery system of claim 21, wherein the patient is a human.

26. A method for treating macular degeneration in a human in need thereof, comprising administering by intravitreal injection into the vitreous chamber of the eye of a patient an effective amount of a drug delivery system which comprises:
(i) microparticles having a diameter of 30 μm or less including a core which consists essentially of the biodegradable polymer polylactide-co-glycolide;
(ii) a coating non-covalently associated with the microparticles, wherein the coating comprises molecules having a polyethylene glycol hydrophilic region and a hydrophobic region, (iii) a therapeutically effective amount of an anti-vascular endothelial growth factor agent,
wherein the drug delivery system provides sustained release of the anti-vascular endothelial growth factor agent into the vitreous chamber over a period of time of at least three months;
wherein the vitreous chamber of the eye exhibits at least 10% less inflammation or intraocular pressure than if the particles were uncoated for at least about 30 days post-administration; and
wherein the drug delivery system is lyophilized and then reconstituted prior to administration by intravitreal injection in a sterile suspension that includes a suspending agent.

27. The method of claim 26, wherein the anti-angiogenic agent is released from the drug delivery system into the vitreous chamber over a period of time of at least six months.

28. The method of claim 26, wherein the patient is a human.

29. An injectable composition for administration to the vitreous chamber of the eye of a patient, comprising a drug delivery system that comprises:
(i) microparticles having a diameter of 30 μm or less including a core which includes the biodegradable polymer polylactide-co-glycolide;
(ii) a coating non-covalently associated with the microparticle; wherein the coating comprises molecules having a polyethylene glycol hydrophilic region and a hydrophobic region;
(iii) a therapeutically effective amount of an anti-vascular endothelial growth factor agent;
(iv) in a sterile suspension suitable for intravitreal delivery that includes a suspending agent;
wherein the drug delivery system provides sustained release of anti-vascular endothelial growth factor agent into the vitreous chamber of the eye over a period of time of at least three months, and
wherein the vitreous chamber of the eye exhibits at least 10% less inflammation or intraocular pressure than if the particles were uncoated for at least about 30 days post-administration.

30. The injectable composition of claim 29, wherein the drug delivery system provides sustained release of the anti-VEGF agent into the vitreous chamber of the eye over a period of time of at least six months.

31. The injectable composition of claim 29, wherein the microparticles consist essentially of polylactide-co-glycolide.

32. The injectable composition of claim 29, wherein the patient is a human.

33. An injectable system for intravitreal injection into the vitreous chamber of the eye of a patient, comprising a drug delivery system that comprises:
(i) microparticles having a diameter of 30 μm or less including a core which includes the biodegradable polymer polylactide-co-glycolide;
(ii) a coating non-covalently associated with the microparticles; wherein the coating is a molecule that has a polyethylene glycol hydrophilic region and a hydrophobic region;
(iii) a therapeutically effective amount of an anti-VEGF agent;
(iv) in a sterile suspension, wherein the sterile suspension includes a suspending agent; and
(v) a device containing a needle for intravitreal injection.

34. The injectable system of claim 33, wherein the microparticles consist essentially of polylactide-co-glycolide.

35. The injectable system of claim 33, wherein the patient is a human.

36. A method for treating an eye disorder in a patient in need thereof, comprising administering by intravitreal injection into the vitreous chamber of the eye an effective amount of a drug delivery system which comprises:
(i) microparticles including a core which includes the biodegradable polymer polylactide-co-glycolide;
(ii) a coating non-covalently associated with the microparticles; wherein the coating comprises molecules having a hydrophilic region and a hydrophobic region, and wherein the hydrophilic region is polyethylene glycol;
(iii) a therapeutically effective amount of an anti-angiogenic agent,
wherein the drug delivery system provides sustained release of the anti-angiogenic agent into the vitreous chamber over a period of time of at least three months; and
wherein the vitreous chamber of the eye exhibits at least 10% less inflammation or intraocular pressure than if the particles were uncoated.

37. The method of claim 36, wherein the microparticles have a diameter of about 50 microns or less.

38. The method of claim 36, wherein the microparticles have a diameter of about 30 microns or less.

39. The method of claim 36, wherein the coating molecule is a block-copolymer.

40. The method of claim 36, wherein the microparticle consists essentially of polylactide-co-glycolide.

41. The method of claim 36, wherein the disorder is macular degeneration.

42. The method of claim 36, wherein the disorder is age-related macular degeneration.

43. The method of claim 36, wherein the disorder is diabetic retinopathy.

44. The method of claim 36, wherein the disorder is corneal neovascularization.

45. The method of claim 36, wherein the anti-angiogenic agent is released from the drug delivery system into the vitreous chamber of the patient's eye over a period of time of at least six months.

46. The method of claim 36, wherein the anti-angiogenic agent is an anti-vascular endothelial growth factor agent.

47. The method of claim 36, wherein the patient is a human.

48. The method of claim 36, wherein the drug delivery system is lyophilized and then reconstituted prior to administration by intravitreal injection.

49. The method of claim 36, wherein the drug delivery system is provided in a sterile suspension.

50. The method of claim 49, wherein the sterile suspension includes a suspending agent.

51. An injectable composition for administration to the vitreous chamber of the eye of a patient, comprising a drug delivery system that comprises:
(i) microparticles having a diameter of 30 µm or less including a core which includes the biodegradable polymer polylactide-co-glycolide;
(ii) a coating non-covalently associated with the microparticles; wherein the coating comprises molecules having a polyethylene glycol hydrophilic region and a hydrophobic region;
(iii) a therapeutically effective amount of an anti-angiogenic agent;
(iv) in a sterile suspension suitable for intravitreal delivery;
wherein the drug delivery system provides sustained release of the anti-angiogenic agent into the vitreous chamber of the eye of the patient over a period of time of at least three months.

52. The injectable composition of claim 51, wherein the composition includes a suspending agent.

53. The injectable composition of claim 51, wherein the anti-angiogenic agent is an anti-vascular endothelial growth factor agent.

54. The injectable composition of claim 51, wherein the drug delivery system provides sustained release of the anti-angiogenic agent into the vitreous chamber of the eye over a period of time of at least six months.

55. The injectable composition of claim 51, wherein the microparticles consist essentially of polylactide-co-glycolide.

56. The injectable composition of claim 51, wherein the patient is a human.

57. An injectable system for intravitreal injection into the vitreous chamber of the eye of a patient, comprising a drug delivery system that comprises:
microparticles having a diameter of 30 µm or less including a core which includes the biodegradable polymer polylactide-co-glycolide;
(ii) a coating non-covalently associated with the microparticles; wherein the coating comprises molecules having a polyethylene glycol hydrophilic region and a hydrophobic region;
(iii) a therapeutically effective amount of an anti-angiogenic agent;
(iv) in a sterile suspension; and
(v) a device containing a needle for intravitreal injection,
wherein the system provides sustained release of the anti-angiogenic agent into the vitreous chamber of the eye patient's over a period of time of at least three months and
wherein the vitreous chamber of the eye exhibits at least 10% less inflammation or intraocular pressure than if the particles were uncoated.

58. The injectable system of claim 57, wherein the microparticles consist essentially of polylactide-co-glycolide.

59. The injectable system of claim 57, wherein the patient is a human.

60. The injectable system of claim 57, wherein the composition includes a suspending agent.

61. The injectable system of claim 57, wherein the anti-angiogenic agent is an anti-vascular endothelial growth factor agent.

62. A method for treating macular degeneration in a human in need thereof, comprising administering by intravitreal injection into the vitreous chamber of the eye of a patient an effective amount of a drug delivery system which comprises:
(i) microparticles having a diameter of 30 µm or less including a core which consists essentially of the biodegradable polymer polylactide-co-glycolide;
(ii) a coating non-covalently associated with the microparticles; wherein the coating comprises molecules having a polyethylene glycol hydrophilic region and a hydrophobic region;
(iii) a therapeutically effective amount of anti-vascular endothelial growth factor agent, wherein the drug delivery system provides sustained release of the anti-vascular endothelial growth factor agent into the vitreous chamber over a period of time of at least three months;

wherein the vitreous chamber of the eye exhibits at least 10% less inflammation or intraocular pressure than if the particles were uncoated; and wherein the drug delivery system is lyophilized and then reconstituted prior to administration by intravitreal injection in a sterile suspension that includes a suspending agent.

63. The method of claim 62, wherein the anti-vascular endothelial growth factor agent is released from the drug delivery system into the vitreous chamber over a period of time of at least six months.

64. The method of claim 62, wherein the patient is a human.

65. An injectable composition for administration to the vitreous chamber of the eye of a patient, comprising a drug delivery system that comprises:
(i) microparticles having a diameter of 30 μm or less including a core which includes the biodegradable polymer polylactide-co-glycolide;
(ii) a coating non-covalently associated with the microparticles; wherein the coating comprises molecules having a polyethylene glycol hydrophilic region and a hydrophobic region;
(iii) a therapeutically effective amount of an anti-vascular endothelial growth factor agent;
(iv) in a sterile suspension suitable for intravitreal delivery that includes a suspending agent;

wherein the drug delivery system provides sustained release of the anti-VEGF agent into the vitreous chamber of the eye over a period of time of at least three months and wherein the vitreous chamber of the eye exhibits at least 10% less inflammation or intraocular pressure than if the particles were uncoated.

66. The injectable composition of claim 65, wherein the drug delivery system provides sustained release of the anti-angiogenic agent into the vitreous chamber of the eye over a period of time of at least six months.

67. The injectable composition of claim 65, wherein the patient is a human.

68. An injectable system for intravitreal injection into the vitreous chamber of the eye of a patient, comprising a drug delivery system that comprises:
microparticles having a diameter of 30 μm or less including a core which includes the biodegradable polymer polylactide-co-glycolide;
(ii) a coating non-covalently associated with the microparticles; wherein the coating comprises molecules having a polyethylene glycol hydrophilic region and a hydrophobic region;
(iii) a therapeutically effective amount of an anti-vascular endothelial growth factor agent;
(iv) in a sterile suspension, wherein the sterile suspension includes a suspending agent; and
(x) a device containing a needle for intravitreal injection.

69. The injectable system of claim 68, wherein the patient is a human.

* * * * *

UNITED STATES PATENT AND TRADEMARK OFFICE
CERTIFICATE OF CORRECTION

PATENT NO. : 9,937,130 B2
APPLICATION NO. : 15/138132
DATED : April 10, 2018
INVENTOR(S) : Peter J. McDonnell et al.

Page 1 of 2

It is certified that error appears in the above-identified patent and that said Letters Patent is hereby corrected as shown below:

In the Specification

Column 3, Line 15, replace the term "stroma or" with --stroma, or--.
Column 3, Line 20, replace the term "drug and" with --drug, and--.
Column 3, Line 51, replace the term "P105 and" with --P105, and--.
Column 3, Line 60, replace the term "drug and" with --drug, and--.
Column 4, Line 49, replace the term "parameters, percentages," with --percentages,--.
Column 5, Line 22, replace the term "for example" with --for example,--.
Column 5, Line 29, replace the term "coating and" with --coating, and--.
Column 5, Line 33, replace the term "example" with --example,--.
Column 8, Line 25, replace the term "polyaklyene oxides" with --polyalkylene oxides--.
Column 9, Line 1, replace the term "greater or" with --greater, or--.
Column 9, Line 7, replace the term "F-108 and F-127" with --F-108, and F-127--.
Column 9, Line 8, replace the term "F-108 and F-127" with --F-108, and F-127--.
Column 9, Line 9, replace the term "F-108 and F-127" with --F-108, and F-127--.
Column 9, Line 10, replace the term "F-108 and F-127" with --F-108, and F-127--.
Column 9, Line 23, replace the term "electrostatic interactions and" with --electrostatic interactions, and--.
Column 9, Line 46, replace the term "In some embodiments" with --In some embodiments,--.
Column 9, Line 50, replace the term "vitamin E and" with --vitamin E, and--.
Column 9, Line 64, replace the term "from about from about" with --from about--.
Column 10, Line 64, replace the term "drugs and" with --drugs, and--.
Column 10, Line 65, replace the term "used the" with --used in the--.
Column 11, Line 24-25, replace the term "tacrolimus and" with --tacrolimus, and--.
Column 11, Line 51, replace the term "glaucoma and" with --glaucoma, and--.
Column 12, Line 35, replace the term "chamber or" with --chamber, or--.
Column 12, Line 61, replace the term "14 and 30" with --14, and 30--.
Column 12, Line 66, replace the term "for example" with --for example,--.
Column 13, Line 5, replace the term "Slit-lamp" with --slit-lamp--.

Signed and Sealed this
Second Day of October, 2018

Andrei Iancu
*Director of the United States Patent and Trademark Office*

CERTIFICATE OF CORRECTION (continued)
U.S. Pat. No. 9,937,130 B2

Column 13, Line 8, replace the term "flare and fibrin" with --flare, and fibrin--.
Column 13, Line 10, replace the term "for example" with --for example,--.
Column 13, Line 10, replace the term "14 and 30" with --14, and 30--.
Column 13, Line 25, replace the term "for example" with --for example,--.
Column 13, Line 50, replace the term "for example" with --for example,--.
Column 15, Line 28, replace the term "and clotrimazole," with --clotrimazole--.
Column 15, Line 41, replace the term "moxifloxacin, and" with --moxifloxacin,--.
Column 18, Line 27, replace the term "antibacterial and/or" with --antibacterial, and/or--.
Column 18, Line 27, replace the term "antifungal and/or" with --antifungal, and/or--.
Column 18, Line 28, replace the term "anti-amoebic and/or" with --anti-amoebic, and/or--.
Column 19, Line 17-18, replace "500 nm or more" with --500 nm, or more--.
Column 19, Line 58, replace "iniranasally" with --intranasally--.
Column 20, Line 23, replace the term "900 and 1000 nm" with --900, and 1000 nm,--.
Column 20, Line 35-36, replace the term "90, and 100 μm" with --90, and 100 μm,--.
Column 23, Line 19, replace the term "treated and" with --treated,--.
Column 24, Line 43, replace the term "making levigating" with --making, levigating--.
Column 24, Line 43, replace the term "entrapping" with --entrapping,--.
Column 24, Line 47, replace the term "excipients or" with --excipients, or--.
Column 24, Line 52, replace the term "solutions or" with --solutions, or--.
Column 24, Line 54, replace the term "stabilizing and/or" with --stabilizing, and/or--.
Column 28, Line 18, replace the term "fluorescence" with --fluorescently--.
Column 29, Line 25, replace the term "flare and fibrin" with --flare, and fibrin--.
Column 30, Line 45, replace the term "PLGA-F127 and" with --PLGA-F127, and--.
Column 30, Line 47, replace the term "PLGA-PVA and" with --PLGA-PVA, and--.
Column 30, Line 49, replace the term "PLGA-F127 and" with --PLGA-F127, and--.

In the Claims

Claim 26, Column 33, Line 67, replace the term "hydrophobic region," with --hydrophobic region; and--.
Claim 29, Column 34, Line 32, replace the term "factor agent;" with --factor agent; and--.
Claim 36, Column 35, Line 16, replace the term "polyethylene glycol;" with --polyethylene glycol; and--.
Claim 51, Column 36, Line 2, replace the term "agent;" with --agent; and--.
Claim 57, Column 36, Line 26, replace the term "microparticles" with --(i) microparticles--.
Claim 62, Column 36, Line 65, replace the term "hydrophobic region;" with --hydrophobic region; and--.
Claim 65, Column 37, Line 29, replace the term "factor agent;" with --factor agent; and--.
Claim 68, Column 38, Line 17, replace the term "microparticles" with --(i) microparticles--.